US008162835B2

(12) United States Patent
Ichikawa et al.

(10) Patent No.: US 8,162,835 B2
(45) Date of Patent: Apr. 24, 2012

(54) ULTRASONIC IMAGE GENERATING METHOD

(75) Inventors: Junichi Ichikawa, Hino (JP); Masahiro Takeda, Hino (JP)

(73) Assignee: Olympus Corporation, Tokyo (JP)

( * ) Notice: Subject to any disclaimer, the term of this patent is extended or adjusted under 35 U.S.C. 154(b) by 861 days.

(21) Appl. No.: 11/280,751

(22) Filed: Nov. 16, 2005

(65) Prior Publication Data
US 2006/0079772 A1 Apr. 13, 2006

Related U.S. Application Data

(63) Continuation of application No. PCT/JP2004/007123, filed on May 19, 2004.

(30) Foreign Application Priority Data

May 19, 2003 (JP) ................................. 2003-140823
Nov. 17, 2003 (JP) ................................. 2003-387281

(51) Int. Cl.
*A61B 8/00* (2006.01)
(52) U.S. Cl. ......... 600/443; 600/437; 600/462; 600/463
(58) Field of Classification Search .................. 600/437, 600/443, 462, 463, 466, 467; 73/1.82, 584, 73/596, 618–631
See application file for complete search history.

(56) References Cited

U.S. PATENT DOCUMENTS

| 5,413,106 | A |   | 5/1995  | Fujita et al. |       |
|-----------|---|---|---------|---------------|-------|
| 5,622,174 | A |   | 4/1997  | Yamazaki      |       |
| 5,817,019 | A |   | 10/1998 | Kawashima     |       |
| 5,830,145 | A | * | 11/1998 | Tenhoff       | 600/463 |
| 5,885,218 | A | * | 3/1999  | Teo et al.    | 600/443 |
| 6,106,466 | A |   | 8/2000  | Sheehan et al. |      |
| 6,152,878 | A | * | 11/2000 | Nachtomy et al. | 600/467 |
| 6,210,328 | B1|   | 4/2001  | Robinson      |       |
| 2002/0122576 | A1 |  | 9/2002  | Weese et al.  |       |

FOREIGN PATENT DOCUMENTS

| EP | 0 802 424 B1 | 10/1997 |
|----|--------------|---------|
| JP | 6-285065     | 10/1994 |
| JP | 6-285066     | 10/1994 |
| JP | 8-332187     | 12/1996 |

(Continued)

OTHER PUBLICATIONS

Leotta, Daniel F. et al., Serial Measurement of Cross-Sectional Area in Peripheral Vein Grafts Using Three-Dimensional Ultrasound, Ultrasound in Med. & Biol., Jan. 1, 2001, pp. 61-68, vol. 27, No. 1.

(Continued)

*Primary Examiner* — Tse Chen
*Assistant Examiner* — Peter Luong
(74) *Attorney, Agent, or Firm* — Scully, Scott, Murphy & Presser, P.C.

(57) ABSTRACT

An ultrasonic image generating method for generating an ultrasonic image based on ultrasonic echo data obtained by transmitting/receiving ultrasonic waves to/from an inspection object, according to the present invention, includes reference position setting steps for determining the reference position on each image with respect to a plurality of consecutive two-dimensional tomograms; correction steps for obtaining regular and consecutive two-dimensional tomograms-by-correcting irregularity of the reference position of each of the two-dimensional tomograms determined by the reference position setting steps; and an ultrasonic image generating step for generating the ultrasonic images based on the regular and consecutive two-dimensional tomograms corrected by the correction steps.

12 Claims, 28 Drawing Sheets

FOREIGN PATENT DOCUMENTS

| | | |
|---|---|---|
| JP | 10-192 | 1/1998 |
| JP | 10-248844 | 9/1998 |
| JP | 2000-254123 | 9/2000 |
| JP | 2000-316864 | 11/2000 |
| JP | 2000-316865 | 11/2000 |
| JP | 3316268 | 6/2002 |
| JP | 2002-204790 | 7/2002 |
| JP | 2002-526226 | 8/2002 |
| WO | WO 00/20886 | 4/2000 |

OTHER PUBLICATIONS

Sanches, Joao M. et al., Joint Image Registration and Volume Reconstruction for 3D Ultrasound, Pattern Recognition Letters, Elsevier, Feb. 1, 2003, pp. 791-800, vol. 24, No. 4-5.

Supplementary European Search Report dated Jul. 6, 2010.

* cited by examiner

ULTRASONIC IMAGE GENERATING METHOD

CROSS REFERENCE TO RELATED APPLICATION

This application is a continuation application of PCT/JP2004/007123 filed on May 19, 2004 and claims benefit of Japanese Applications No. 2003-140823 filed in Japan on May 19, 2003 and No. 2003-387281 filed in Japan on Nov. 17, 2003, the entire contents of which are incorporated herein by this reference.

BACKGROUND OF THE INVENTION

1. Field of the Invention

The present invention relates to an ultrasonic image generating method for generating an ultrasonic image based on ultrasonic echo data obtained by transmitting/receiving ultrasonic waves to/from an inspection object.

2. Description of the Related Art

In recent years, ultrasonic diagnostic apparatuses have come into wide use in medical and industrial fields. The ultrasonic diagnostic apparatuses are for noninvasively diagnosing the inside of an inspection object by transmitting/receiving ultrasonic waves to/from the inspection object.

These conventional ultrasonic diagnostic apparatuses are provided with an ultrasonic image generating method for generating an three-dimensional ultrasonic (cubic) image constructed by two-dimensional tomograms, such as radial images (cross sections perpendicular to the scan axis of an ultrasonic transducer) and linear images (cross sections horizontal to the scan axis of the ultrasonic transducer), based on ultrasonic echo data obtained by transmitting/receiving ultrasonic waves to/from the inspection object.

As such a conventional ultrasonic image generating method, for example, as shown in Japanese Unexamined Patent Application Publication No. 2000-254123, a method has been proposed by which a three-dimensional image extracted from a body cavity surface is generated in order to facilitate three-dimensionally recognizing an ultrasonic image.

In general, one problem associated with a tomogram is the "pulsation" of a human body.

Typically, the ultrasonic diagnostic apparatus performs a helical scan by causing the ultrasonic transducer to radially scan (i.e., scan perpendicularly to the scan axis of the ultrasonic transducer), and causing it to linearly scan (i.e., scan horizontally to the scan axis of the ultrasonic transducer), and thereby acquires two-dimensional tomograms such as the above-described radial image and linear image. Here, the helical scan requires a time of, e.g., about 2 to 4 sec.

However, in the above-described conventional ultrasonic image generating method, the positions of a region of interest usually causes deviation between the scan starting time and scan finishing time due to the pulsation occurring for the time period of about 2 to 4 sec during which the above-described helical scan is performed. This "deviation" causes a problem chiefly in the above-described linear image. When the extent of the deviation is too large, even if the linear image is constructed, it may not bring about a clear image.

Possible causes of the deviation in the linear image include elements shown in the following table 1 besides the pulsation.

TABLE 1

| Causes | Features |
| --- | --- |
| Pulsation | About 70 times per min; periodic, small, and vigorous movement |
| Peristalsis | On the order of once every several seconds; periodic, large, and slow movement |
| Fluctuation of Probe | Irregular and slow movement |
| Respiratory Movement | Irregular and slow movement |

The ultrasonic image generating method set forth in the above-described Japanese Unexamined Patent Application Publication No. 2000-254123 involves a problem in that, when the images of an organ with blood vessels running adjacently thereto are converted into a three-dimensional image, the organ shifts under the influence of the pulsation, thereby distorting the image.

In contrast to this, among the conventional ultrasonic image generating methods, a method has been proposed that attempts to eliminate the influence of the pulsation, for example, as set forth in Japanese Unexamined Patent Application Publication No. 2000-316864.

However, the ultrasonic image generating method set forth in the above-described Japanese Unexamined Patent Application Publication No. 2000-316864 has attained an effect to a certain extent on the elimination of pulsation, but the elimination effect thereof is not yet sufficient. This being the situation, a more effective ultrasonic image generating method has been demanded.

On the other hand, among the conventional ultrasonic image generating methods, a method has been proposed that attempts to stabilize ultrasonic images by determining the barycenter of a body cavity, as set forth in Japanese Patent No. 3316268.

However, the ultrasonic image generating method set forth in the above-described Japanese Patent No. 3316268 has only the effect of stabilizing two-dimensional tomograms on a monitor, and even if this method is as-is applied to an ultrasonic image with a three-dimensional spread (i.e., three-dimensional image) for eliminating the influence of pulsation, it would produce no effect.

The present invention has been made in light of the above-described situations, and aims to provide an ultrasonic image generating method capable of eliminating the influence of pulsation and acquiring high-quality ultrasonic images.

SUMMARY OF THE INVENTION

An ultrasonic image generating method for generating an ultrasonic image based on ultrasonic echo data obtained by transmitting/receiving ultrasonic waves to/from an inspection object, according to the present invention, includes a reference position setting step for determining the reference position on each image with respect to a plurality of consecutive two-dimensional tomograms; a correction step for obtaining regular and consecutive two-dimensional tomograms by correcting irregularity of the reference position of each of the two-dimensional tomograms determined by the reference position setting step; and an ultrasonic image generating step for generating the ultrasonic images based on the regular and consecutive two-dimensional tomograms corrected by the correction step.

DETAILED DESCRIPTION OF THE PREFERRED EMBODIMENT(S)

Figure 1:
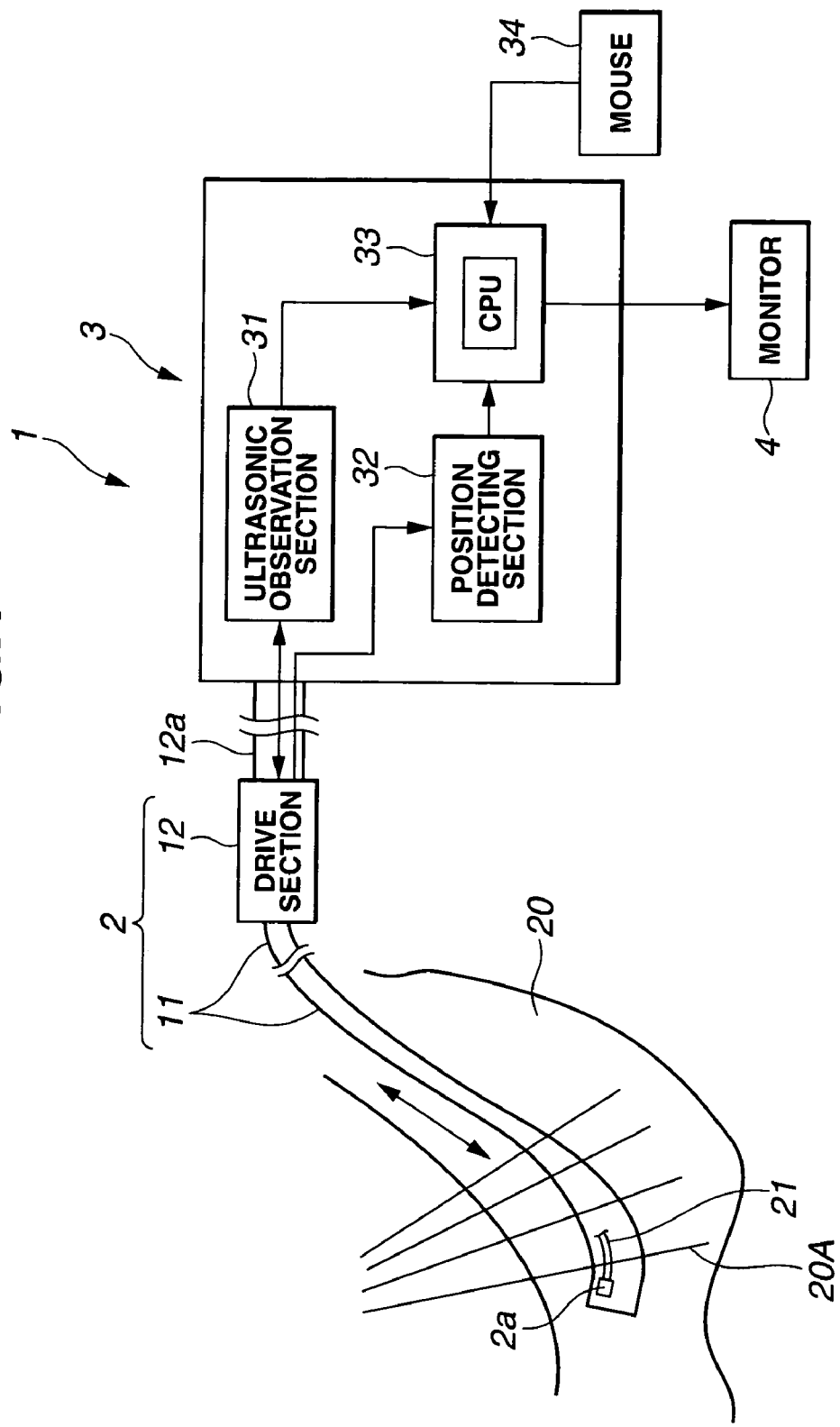
FIG. 1 is a block diagram showing the overall configuration of an ultrasonic diagnostic system according to a first embodiment of the present invention.

As shown in FIG. 1, an ultrasonic diagnostic system 1 according to a first embodiment includes, in the main section thereof, an ultrasonic probe 2 incorporating therein an ultrasonic transducer 2a described later; the apparatus main body (ultrasonic image processing apparatus) 3 for generating an ultrasonic image by signal-processing ultrasonic echo signals received by the ultrasonic probe 2; and a monitor 4 for displaying ultrasonic images in real time by inputting output image signals outputted from the apparatus main body 3.

The ultrasonic probe 2 includes an elongated, flexible insertion section 11 that can be inserted into a body cavity; a drive section 12 to which the proximal end of the insertion section 11 is detachably connected. The insertion section 11 incorporates, in its distal end section 11a, an ultrasonic transducer 2a for transmitting/receiving ultrasonic waves to/form this distal end section 11a.

The ultrasonic transducer 2a is attached to the distal end of a flexible shaft 21. Here, in the ultrasonic probe 2, its distal end section 11a is covered with an acoustic cap transmitting ultrasonic waves. The surroundings of the ultrasonic transducer 2a are filled with ultrasonic propagation media (not shown) transmitting (propagating) ultrasonic waves. A signal line (not shown) extends from the ultrasonic transducer 2a, and is connected to an ultrasonic observation section 31 described later in the apparatus main body 3 via the drive section 12.

The ultrasonic probe 2 is adapted to drive a first motor (not shown) incorporated in the drive section 12 to rotationally drive the ultrasonic transducer 2a, so that the ultrasonic transducer 2a performs radial scans. Furthermore, the ultrasonic probe 2 is adapted to drive a second motor (not shown) incorporated in the drive section 12 to reciprocate the flexible shaft 21 in the axial direction (i.e., longitudinal direction; for example, referred to as a Z-axis direction) of the insertion section 11, so that the ultrasonic transducer 2a can reciprocate and perform a linear scan.

Specifically, the ultrasonic probe 2 rotationally drives the first and second motors in the drive section 12 simultaneously by synchronizing them, so that the ultrasonic transducer 2a can transmit/receive ultrasonic waves in a spiral manner, and perform a helical scan a three-dimensional region in an inspection object. As a result, the apparatus main body 3 can obtain a large number of two-dimensional tomograms varying in the coordinate position in the Z-axis direction from one position to another, little by little, and thereby an ultrasonic image (three-dimensional image) can be constructed from these two-dimensional tomograms.

In the ultrasonic probe 2, its drive section 12 is connected to the apparatus main body 3 by the cable 12a.

The apparatus main body 3 comprises the ultrasonic observation section 31 that transmits/receives ultrasonic signals to/from the ultrasonic transducer 2a to obtain ultrasonic echo data in a three-dimensional region; a position detecting section 32 for obtaining position data on the distal end section 11a of the ultrasonic probe 2 in a body cavity (e.g., stomach 20); an image processing section 33 that is used for obtaining ultrasonic image data based on data by the position detecting section 32 and ultrasonic observation section 31, that specifies the position of a radial scan surface by associating position data from the position detecting section 32 with two-dimensional tomograms, and that has a CPU generating an ultrasonic image (three-dimensional image) based on an ultrasonic image generating method and ultrasonic image generating program each described later.

Figure 2:
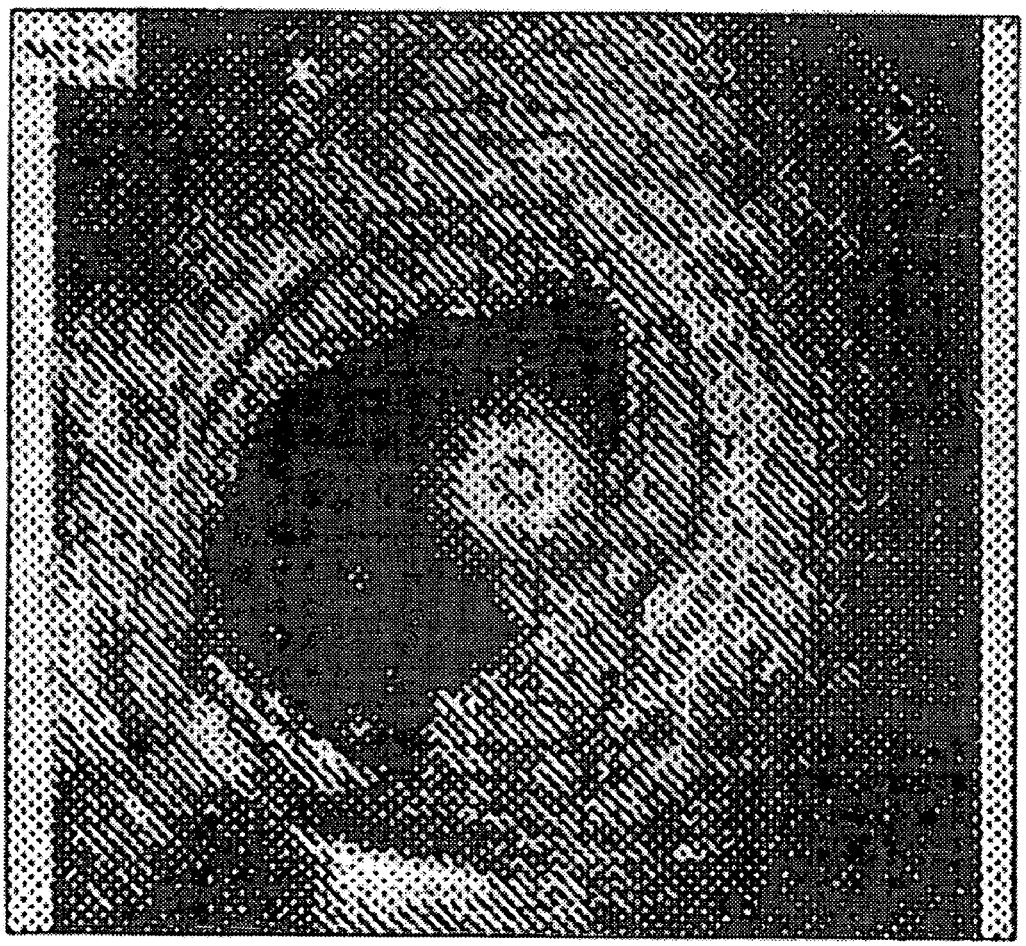
FIG. 2 is a representation of concrete examples of two-dimensional tomograms (radial images) Gr.
Figure 3:
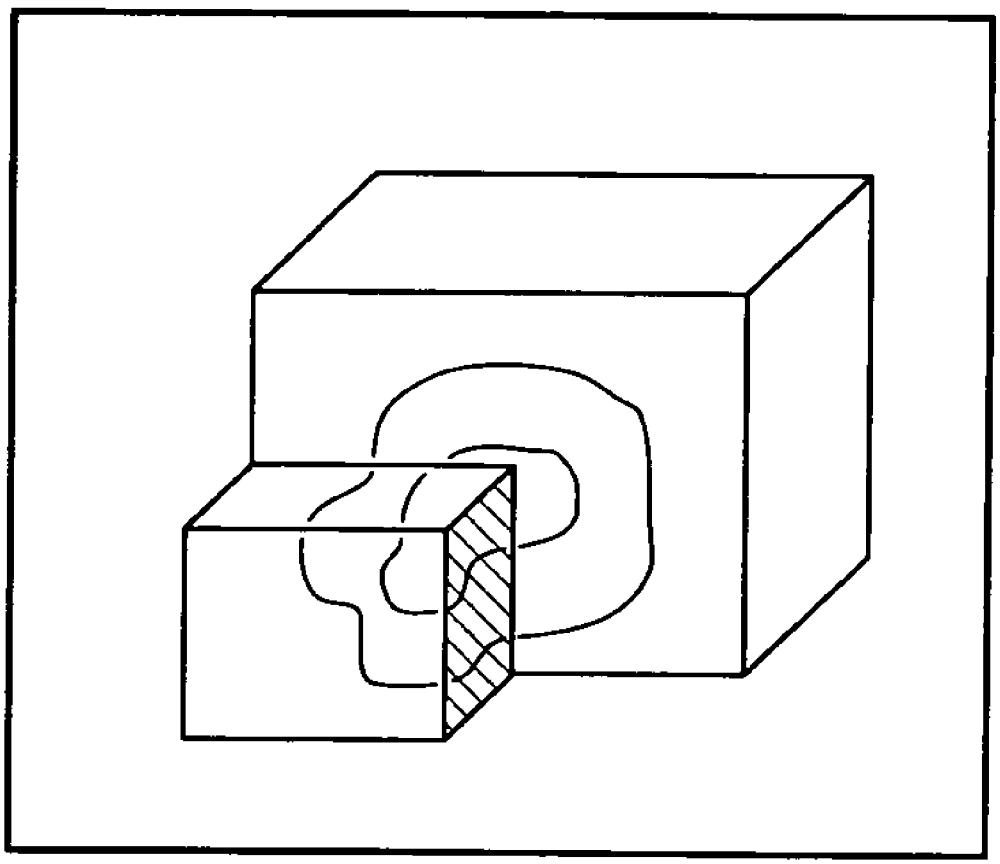
FIG. 3 is a schematic view of an ultrasonic image (three-dimensional image) Gs.

Connected to the image processing section 33 through an interface (not shown), is a mouse 34 serving as screen operating means for allowing images as shown in FIGS. 2 and 3 to be operated in an interactive manner. The mouse 34 has a function of performing a screen operation using a mouse cursor with respect to image information displayed on the display screen of the monitor 4.

The image processing section 33 has a function as control means for moving a selected operation object relative to the movement of the mouse 34, based on the selection of the operation object in a screen operation by the mouse 34. Also connected to the image processing section 33, is a large-capacity external storage device (not shown) for recording image data or the like via an interface (not shown).

The image processing section 33 performs helical scans on the transducer 2a in predetermined pitch units; coordinate-converts ultrasonic echo data obtained in the ultrasonic observation section 31; and generates a plurality of two-dimensional tomograms (hereinafter referred to as radial images) Gr of cross sections substantially perpendicular to the axial direction (Z-axis direction) of the insertion section 11, as shown in FIG. 2. These generated radial images Gr correspond to, for example, ultrasonic tomographic planes 20A in a stomach 20 shown in FIG. 1.

Then, the image processing section 33 generates a pseudo ultrasonic image (three-dimensional image) Gs as shown in FIG. 3 by associating a plurality of radial images Gr consecutively obtained in predetermined pitch units with position data on the distal end section 11a of the ultrasonic probe 2, the position data having been detected in the position detecting section 32.

Here, however, the organ moves under the influence of pulsation, resulting in a distorted ultrasonic image (three-dimensional image) Gs.

With this being the situation, in this embodiment, the influence of pulsation is eliminated by the ultrasonic image generating method and ultrasonic image generating program described below.

Figure 4:
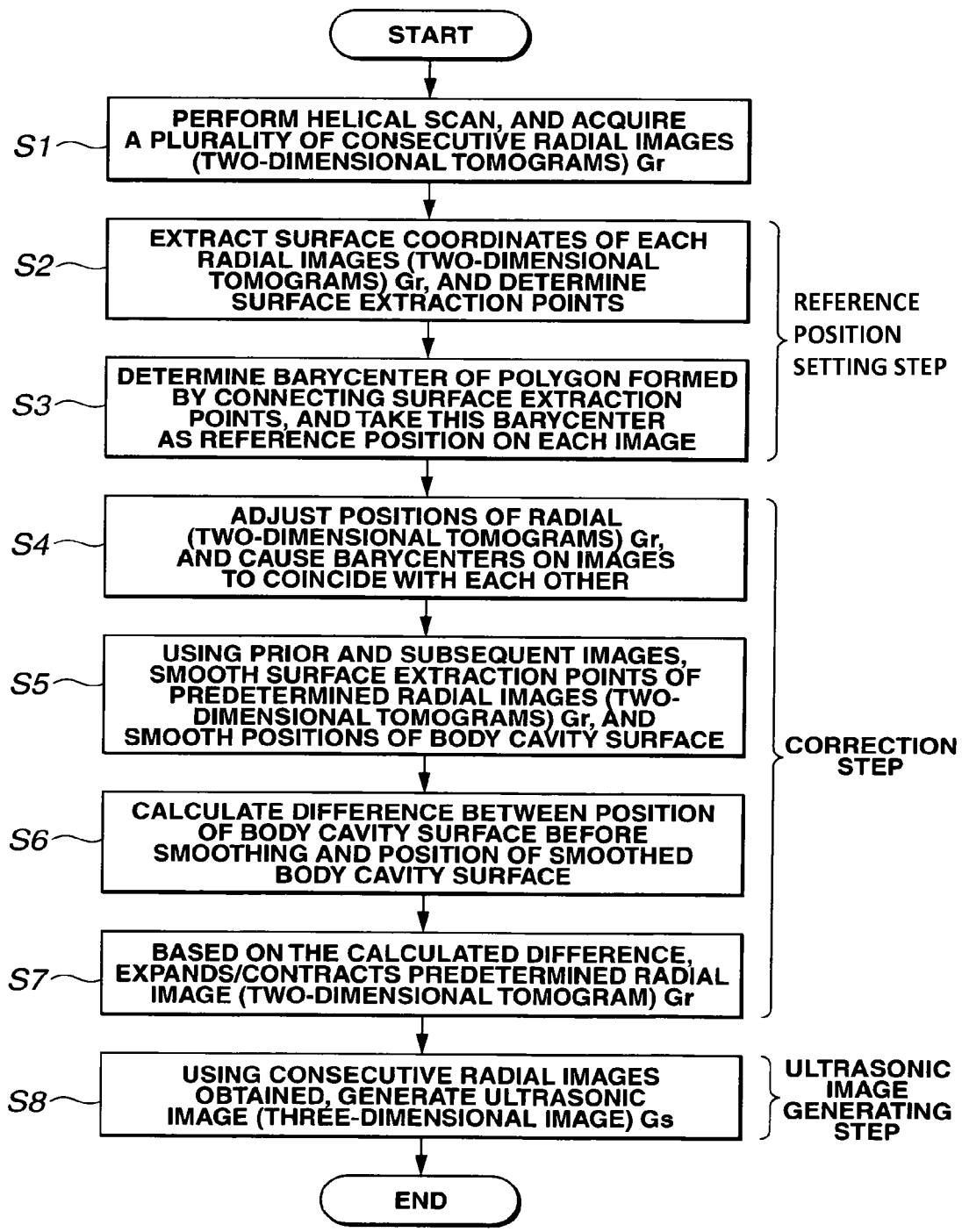
FIG. 4 is a flowchart showing an ultrasonic image generating method in the ultrasonic diagnostic system according to the first embodiment.

With reference to FIGS. 5 to 11, these ultrasonic image generating method and ultrasonic image generating program will be explained based on a flowchart shown in FIG. 4.

First, as described in FIG. 1, the ultrasonic probe 2 rotationally drives the first and second motors in the drive section 12 simultaneously by synchronizing them, so that the ultrasonic transducer 2a performs helical scans in predetermined pitch units.

Thereupon, in the apparatus main body 3, ultrasonic echo signals in a three-dimensional region received by the ultrasonic transducer 2a are inputted into the ultrasonic observation section 31. The ultrasonic observation section 31 receives the ultrasonic echo signals in the three-dimensional region, from the ultrasonic transducer 2a, and coordinate-converts these ultrasonic echo signals to generate a plurality of consecutive radial images Gr. Then, the image processing section 33 receives input of the pieces of image data on the radial images Gr from the ultrasonic observation section 31 one after another, thereby acquiring the plurality of consecutive radial images Gr (step S1).

Simultaneously, the position detecting section 32 acquires position data on the distal end section 11a of the ultrasonic probe 2 in the body cavity, and outputs the acquired pieces of position data to the image processing section 33, one after another.

Then, the image processing section 33 specifies the position of a radial scan surface by associating each piece of position data from the position detecting section 32 with a respective one of the plurality of consecutive radial images Gr.

Then, as reference position setting step for determining the reference position on each image with respect to the plurality of consecutive radial images Gr, the image processing section 33 performs the following processes of steps S2 and S3.

First, with respect to the plurality of consecutive radial images Gr, the image processing section 33 extracts surface coordinates of each of the images, and determines surface extraction points (step S2).

Figure 5:
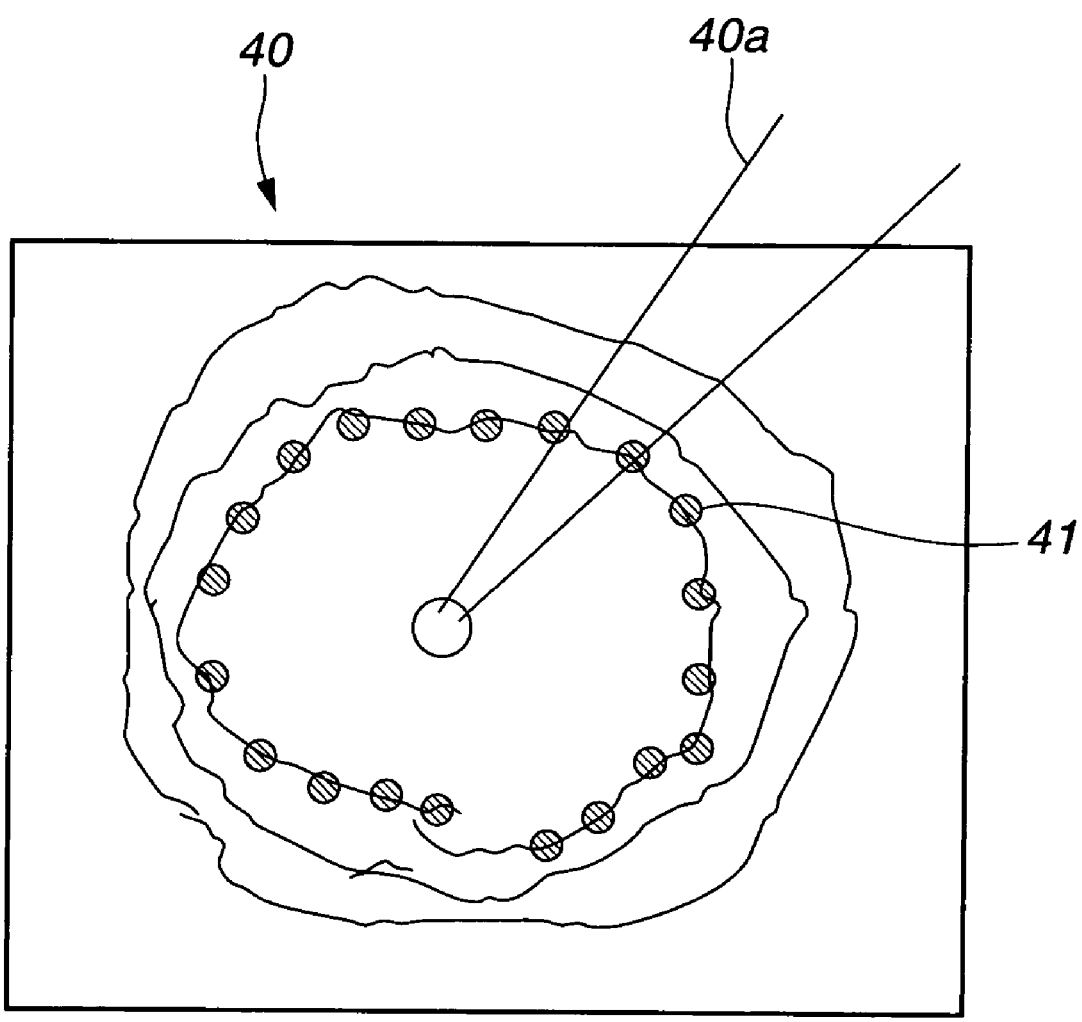
FIG. 5 is a diagram showing images when determining surface extraction points by extracting surface coordinates.

Here, for example, in an image 40 shown in FIG. 5, the image processing section 33 issues search lines 40a from the image center, and extracts portions each exhibiting a large luminance change as surface coordinates, thereby determining the surface extraction points 41.

Next, the image processing section 33 determines a barycenter as a reference position on each of the images with respect to a plurality of consecutive radial images Gr (step S3).

Figure 6:
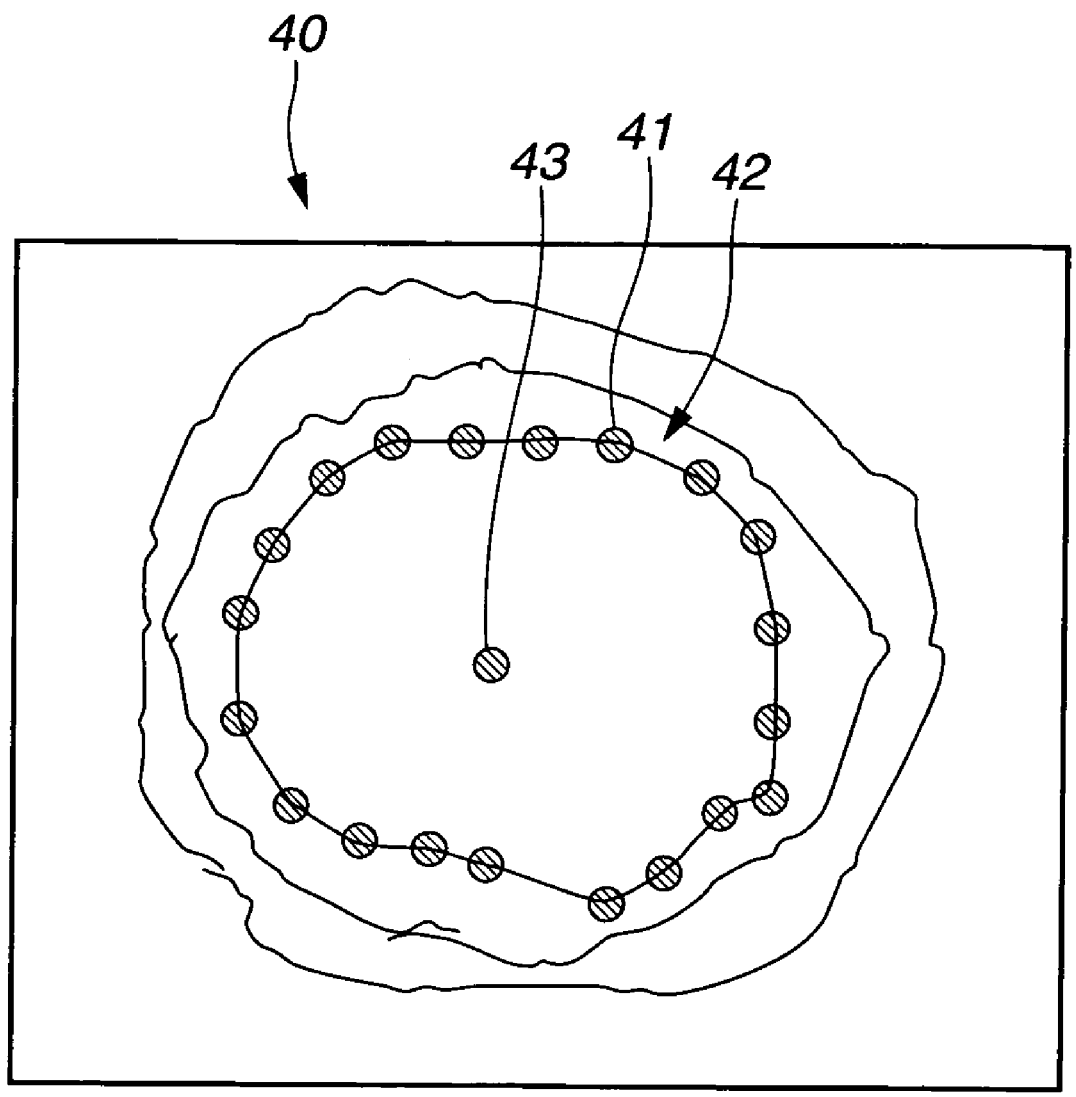
FIG. 6 is a diagram showing images when determining a barycenter by generating a polygon formed by connecting surface extraction points.

Here, for example, the image processing section 33 generates a polygon 42 formed by connecting surface extraction points 41 as shown in FIG. 6, and determines a barycenter 43.

Generally, the barycenters of the polygon 42 include a physical barycenter and geometric barycenter.

In this embodiment, the barycenter 43 of the polygon is determined by a physical barycenter thereof. However, the barycenter 43 may also be determined by a geometric barycenter.

Also, after having generated the polygon 42, the image processing section 33 may approximate the polygon 42 by a circle (not shown) in which the polygon 42 is substantially inscribed, and may determine the center point of this circle as a barycenter.

Next, as correction steps for acquiring consecutive radial images Gr by correcting irregularities of the barycenters 43 with respect to the respective radial images Gr determined in the reference position setting steps (S2 and S3), the image processing section 33 performs the following processes of steps S4 to S7.

Figure 7:
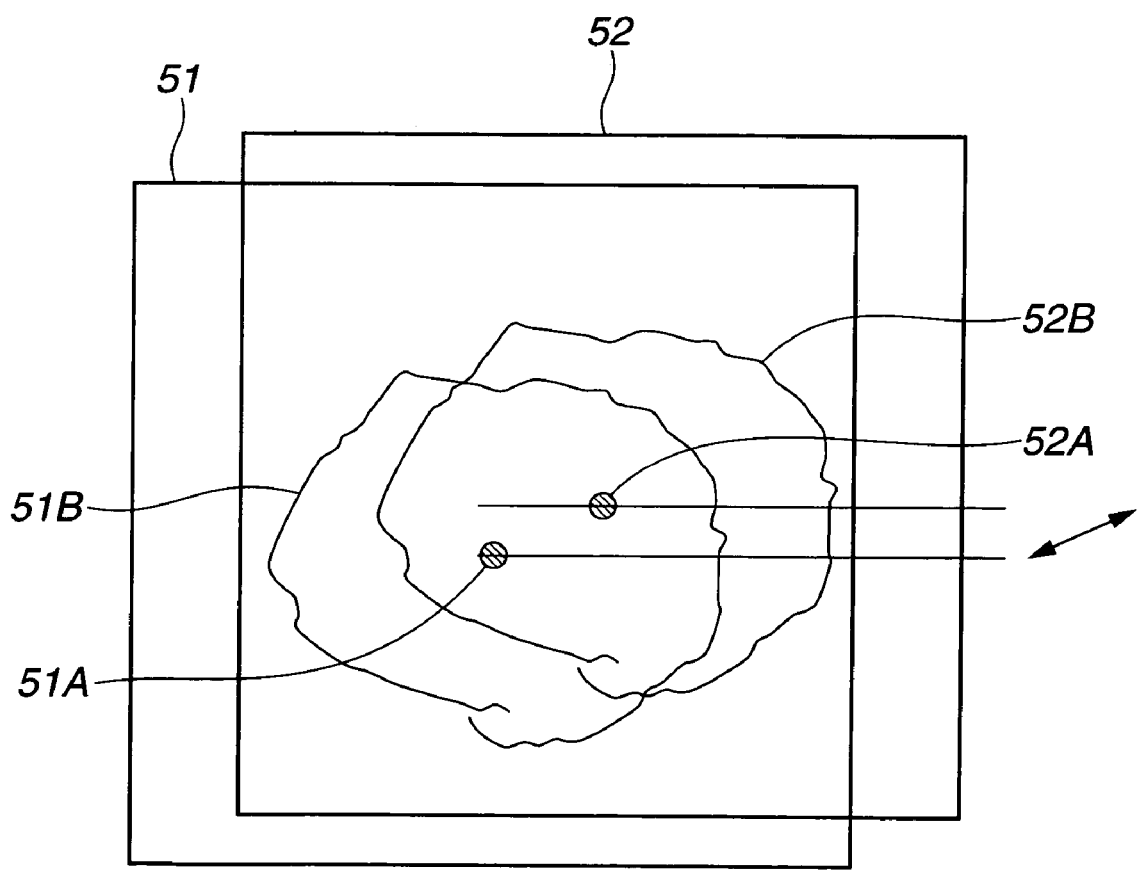
FIG. 7 is a diagram showing two images when corresponding positions on the body cavity surface on the two radial images are mutually deviated between the two radial images even though these images depict the same body cavity.

Here, under the influence of pulsation and/or due to mechanical shakes of the probe itself, the plurality of consecutive radial images Gr deviates from each other, for example, as shown in FIG. 7.

As shown in FIG. 7, even though a radial image Gr 51 and radial image Gr 52 depict the same body cavity, the positions of body cavity surfaces 51B and 52B deviate from each other.

Hence, in this embodiment, the image processing section 33 performs processing for shifting each of the plurality of radial images Gr to adjust the positions of these images, and thereby causing the barycenters on the images determined in S3 to coincide (align) with each other (step S4).

Figure 8:
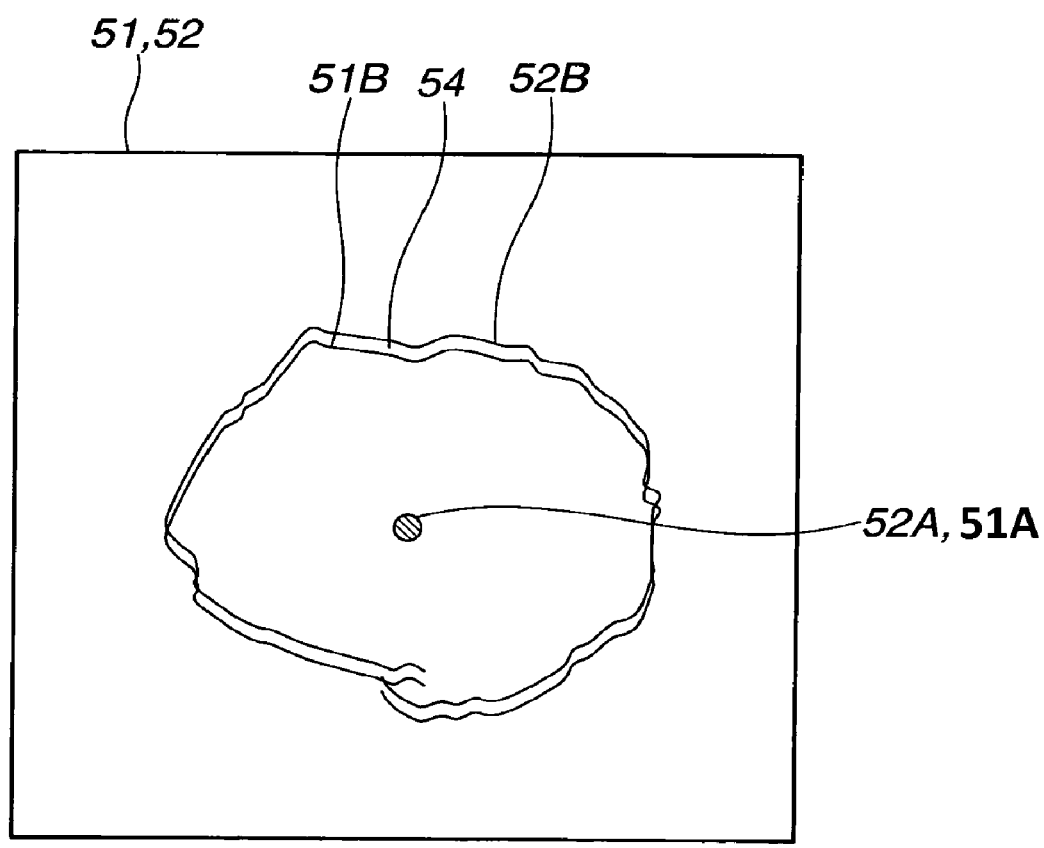
FIG. 8 is a diagram showing two images when barycenters of the two radial images are caused to coincide with each other by adjusting the positions of these images.

For example, as shown in FIG. 8, the image processing section 33 adjusts the positions of the radial image Gr 51 and radial image Gr 52 by shifting their positions in up-and-down and left-and right directions, thereby causing the barycenters 51A and 52A to coincide with each other.

At this time, the image processing section 33 may shift the image positions of the radial image Gr 52 in the up-and-down and left-and-right directions while fixing the image positions of the radial image Gr 51 specified by the user, and vice versa. Thereby, the image processing section 33 can reduce big "fluctuations" due to mechanical factor.

However, the image shown in FIG. 8 still leaves small fluctuations 54.

Hence, the apparatus main body 3 uses prior and subsequent images to perform processing for smoothing the surface extraction points of a predetermined radial image Gr sandwiched by these images, and thereby smoothing the positions of a body cavity surface (step S5).

Here, the image processing section 33 determines the number of pieces of data to be referred to, for smoothing, using the following expression (1):

(Count of pieces of data)=1/pitch×4     (1)

Here, the term "pitch" refers to the distance between two-dimensional tomograms (radial images Gr).

For example, for 0.25 mm pitch, the count of pieces of reference data for smoothing is 16, and for 1 mm pitch, the above-described count is 4.

Also, the image to be referred to is determined by the following expression (2):

(number of the image to be referred to)=(number of a target image)+[n−(count of the reference images)/2]     (2)

Here, n is a numeral value starting from 1 and ending at [(count of reference images)−1].

For example, let the total count of images be 10 (No. 0 to No. 9), and the pitch be 1 mm pitch (i.e., 4 images are referred to for smoothing). Here, when smoothing is applied to No. 5, the images to be referred to are Nos. 3, 4, 5, and 6.

As described above, the image processing section 33 uses prior and subsequent images to smooth the surface extraction points of a predetermined radial image Gr sandwiched by these images, and thereby smoothes the positions of the body cavity surfaces.

Figure 9:
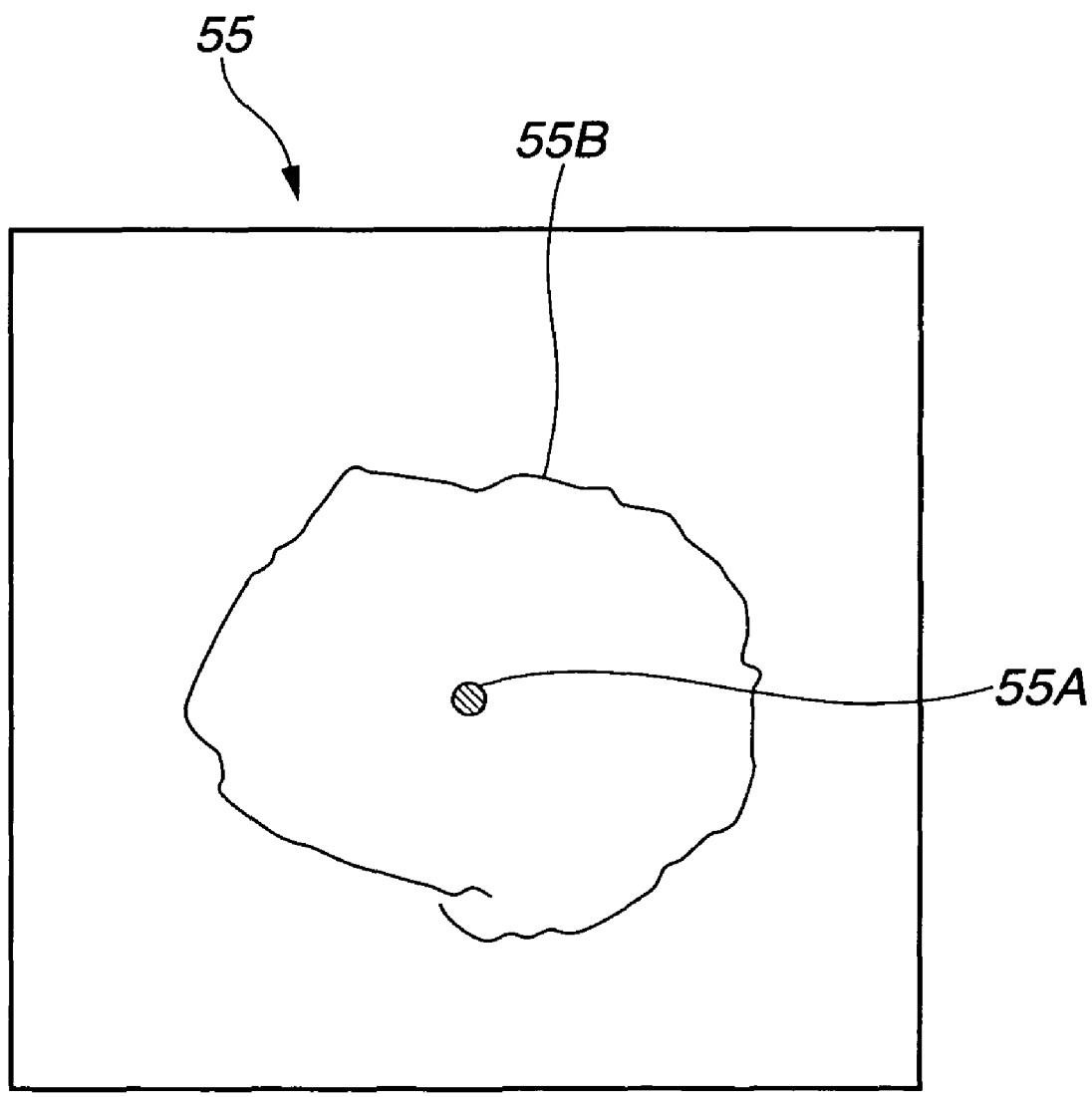
FIG. 9 is a diagram showing an image when a body cavity surface has become smooth as a result of the smoothing.

Then, as the result of the above-described smoothing by the image processing section 33, for example, as shown in FIG. 9, the image 55 constituted of the radial image Gr 51 and radial image Gr 52 becomes smoothed in the body cavity surface 55B thereof. Here, the reference character 55A denotes the barycenter of the image 55.

Figure 10:
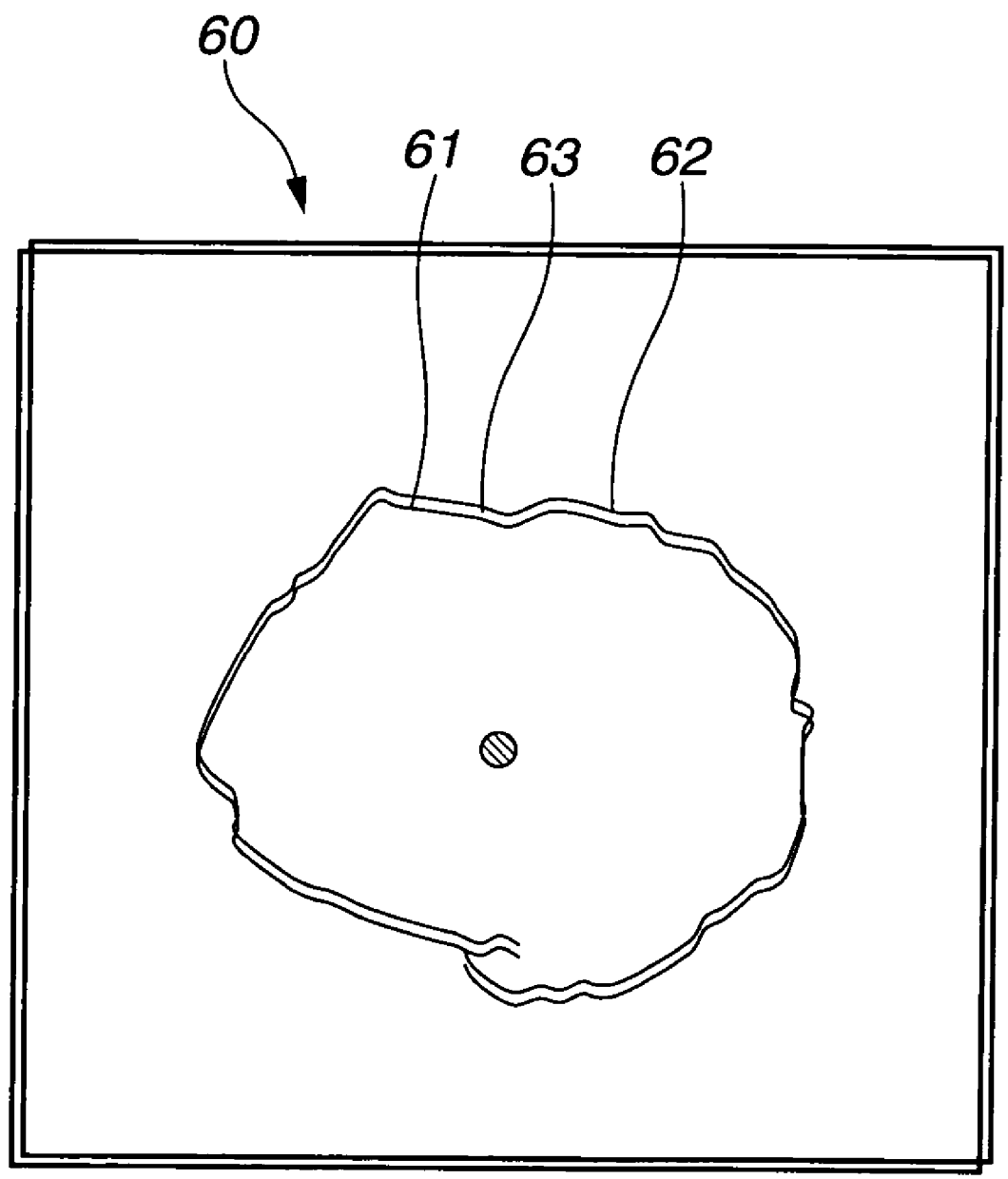
FIG. 10 is a diagram showing images when corresponding surface positions of the body cavity surfaces do not coincide between before and after the smoothing.

Here, regarding the radial image Gr, for example, as in the case of an image 60 shown in FIG. 10, there is a case where the surface positions of the body cavity surface 61 before smoothing (i.e., the positions of an extracted body cavity surface), and the surface positions of the smoothed body cavity surface 62 do not coincide. Here, the reference character 63 denotes the difference between the surface position of the body cavity surface 61 before smoothing (i.e., the position of the extracted body cavity surface) and the surface position of the smoothed body cavity surface 62.

Figure 11:
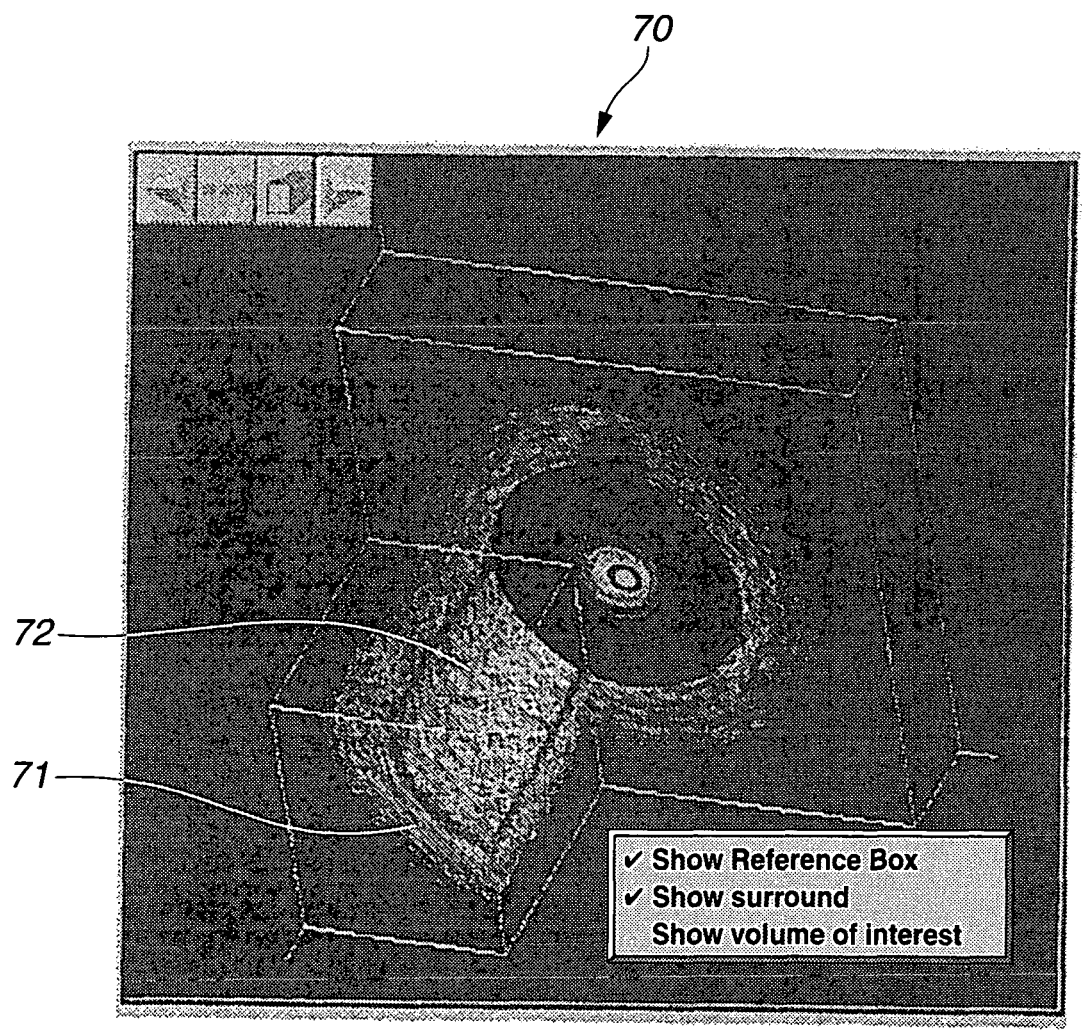
FIG. 11 is a representation of a concrete example of an ultrasonic image (three-dimensional image) Gs.

At this time, for example, in an ultrasonic image (three-dimensional image) Gs 70 shown in FIG. 11, a side cross-section 71 thereof cannot be generated from radial-images Gr in accordance with a smoothed body cavity surface.

It is therefore necessary to deform the image 60 shown in FIG. 10 so that the surface positions of the body cavity surface 61 before smoothing (i.e., the position of the extracted body cavity surface) and the surface positions of the smoothed body cavity surface 62 mutually coincide.

Accordingly, the image processing section 33 now performs processing for calculating the differences between the surface positions of the body cavity surface before smoothing (i.e., the positions of the extracted body cavity surface) and the surface positions of the smoothed body cavity surface, and then performs processing for expanding/contracting a predetermined radial image Gr based on the above-described calculated differences (steps S6 and S7).

Here, in the radial image Gr 60 shown in FIG. 10, the image processing section 33 calculates the differences 63 between the positions of the body cavity surface 61 before smoothing (i.e., the positions of the extracted body cavity surface) and the positions of the smoothed body cavity surface 62, and expands/contracts the image, based on the above-described calculated differences 63.

This allows the image processing section 33 to generate a radial image Gr capable of being conformed to the body cavity surface after the smoothing.

Then, the image processing section 33 acquires consecutive radial images Gr corrected in correction steps (S4 to S7), and associates these consecutive radial images Gr with position data detected by the position detecting section 32 based on the above-described consecutive radial images Gr, whereby the image processing section 33 performs an ultrasonic image generating step (step S8) for generating an ultrasonic image (three-dimensional image) Gs.

Thus, the image processing section 33 can generate an ultrasonic image (three-dimensional image) Gs with the body cavity surface 72 being smooth as shown in FIG. 11.

In the ultrasonic image generating method and ultrasonic image generating program according to the first embodiment, the above-described smoothing processing in step S5 and expanding/contraction processing in step S7 have been described by assuming the Cartesian coordinate system.

Figure 12:
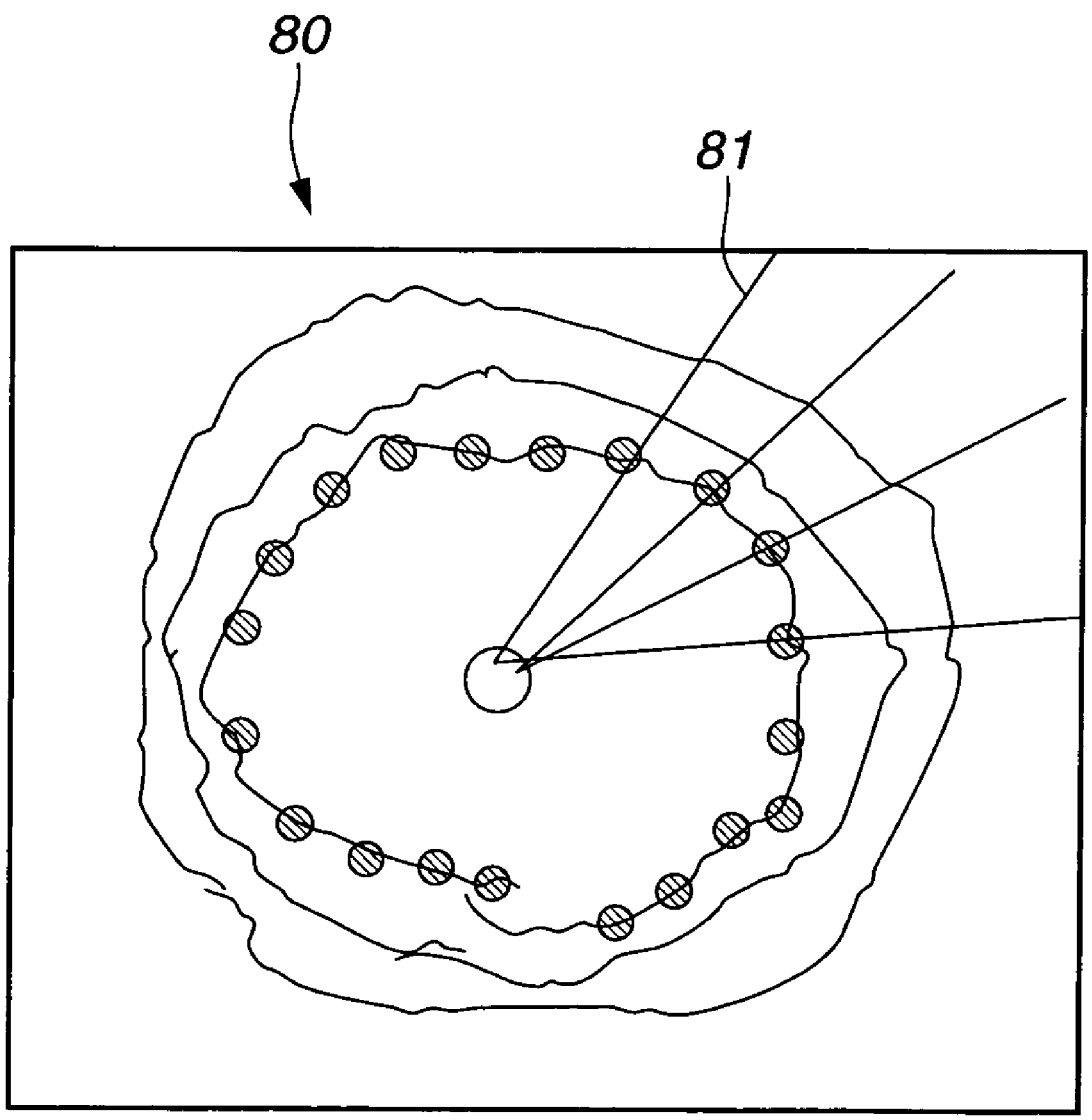
FIG. 12 is a diagram showing that radial images Gr are each formed of several hundred pieces of sound ray data.

However, intrinsically, the radial image Gr, as raw data on ultrasonic echo data, is formed of, for example, sound ray data 81 comprising several hundreds of sound rays, as in an image 80 shown in FIG. 12, and represented by an echo luminance of the sound ray data 81.

Therefore, the above-described smoothing processing in step S5 and expanding/contraction processing in step S7 are easier to perform with a polar coordinate system, with the center of the radial image Gr used as an origin, than with a Cartesian coordinate system.

Hence, the image processing section 33 may treat the above-described smoothing processing and expanding/contraction processing with the polar coordinate system, with the radial image Gr left in the form of sound ray data, while not illustrated.

In this case, for example, when the image processing section 33 subjects the sound ray data to DSC by a digital scan converter (i.e., processing for converting polar coordinate system data generated by radial scans into image data in the Cartesian coordinate system), to convert the sound ray data into the Cartesian coordinate system, the image processing section 33 performs moderate expanding/contraction processes for each of the sound ray data so that positions of extracted body cavity surface align with polygon surface (positions of body cavity surface after smoothing).

More specifically, the image processing section 33 performs expanding/contraction processing by incorporating the influence of smoothing (i.e., the distance differences before and after the smoothing, corresponding to the above-described difference 63 in the surface position in S6), into a sound ray distance determined from a coordinate conversion table for sound ray data.

The ultrasonic image generating method and the ultrasonic image generating program according to the first embodiment can be utilized not only during an ultrasonic inspection, but also when stored data is reproduced after the ultrasonic inspection for an image review for a therapeutic policy in the future, or for volume measurement.

The ultrasonic image generating method and ultrasonic image generating program according to the first embodiment is configured to obtain position data on the distal end section 11a of the ultrasonic probe 2 by the position detecting section 32. However, the present invention is not limited to this. Even when ultrasonic echo data in a three-dimensional region is manually acquired in a pseudo manner, and as an ultrasonic image, is subjected to a three-dimensional display (perspective surface construction displaying a body cavity surface, or a perspective construction without displaying the surface), the ultrasonic image generating method and ultrasonic image generating program according to the present invention can be used to effectively improve the image quality.

As a result, the ultrasonic image generating method and ultrasonic image generating program according to the first embodiment can acquire high-quality and distortion-free two-dimensional tomograms and ultrasonic images (three-dimensional images) that are unsusceptible to pulsation and mechanical shakes of the probe itself.

Next, a second embodiment according to the present invention will be described.

The above-described first embodiment is constructed so as to generate the polygon 42 formed by connecting the surface extraction points 41 as reference positions on each image with respect to a plurality of consecutive radial images Gr, to thereby determine a barycenter 43, whereas the second embodiment is constructed so as to convert the body cavity surface as reference positions on each image, from the polar coordinates into Cartesian coordinates, and determine a body cavity surface center based on four extraction points disposed clockwise at the positions of 3, 6, 9, and 12 o'clock on the above-described Cartesian coordinates. Because other constituents are the same as those in the first embodiment, the description thereof is omitted. The same constituent is designated by the same reference character.

Figure 13:
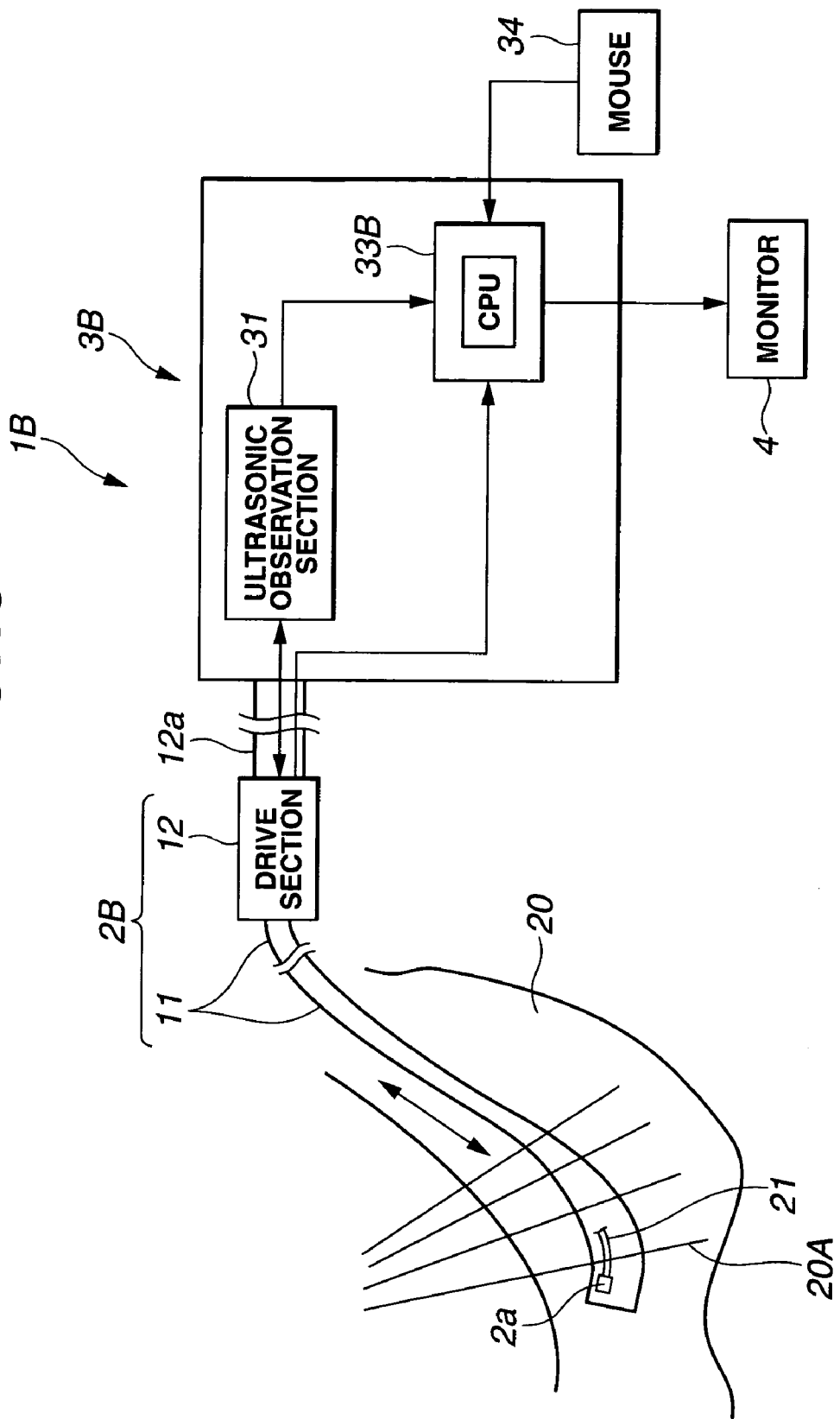
FIG. 13 is a block diagram showing the overall configuration of an ultrasonic diagnostic-system-according to a second embodiment of the present invention.

As shown in FIG. 13, an ultrasonic diagnostic system 1B according to the second embodiment includes, in the main section thereof, an ultrasonic probe 2B incorporating therein an ultrasonic transducer 2a; the apparatus main body (ultrasonic image processing apparatus) 3B for generating an ultrasonic image by signal-processing an ultrasonic echo signal received by the ultrasonic probe 2B; and a monitor 4 for displaying ultrasonic images in real time by inputting output image signals outputted from the apparatus main body 3B.

The ultrasonic probe 2B includes an elongated, flexible insertion section 11 that can be inserted into a body cavity; a drive section 12 to which the proximal end of the insertion section 11 is detachably connected. The insertion section 11 incorporates, in its distal end section 11a, an ultrasonic transducer 2a for transmitting/receiving ultrasonic waves to/form this distal end section 11a.

The ultrasonic transducer 2a is attached to the distal end of a flexible shaft 21. Here, in the ultrasonic probe 2B, its distal end section 11a is covered with an acoustic cap that transmits ultrasonic waves. The surroundings of the ultrasonic transducer 2a are filled with ultrasonic propagation media (not shown) that transmit (propagate) ultrasonic waves. A signal line (not shown) extends from the ultrasonic transducer 2a, and is connected to an ultrasonic observation section 31 in the apparatus main body 3B via the drive section 12.

The ultrasonic probe 2B is adapted to drive a first motor (not shown) incorporated in the drive section 12 to rotationally drive the ultrasonic transducer 2a, so that the ultrasonic transducer 2a performs radial scans. Furthermore, the ultrasonic probe 2B is adapted to drive a second motor (not shown) incorporated in the drive section 12 to reciprocate the flexible shaft 21 in the axial direction (i.e., longitudinal direction; for example, referred to as a Z-axis direction) of the insertion section 11, so that the ultrasonic transducer 2a can reciprocate and perform a linear scan.

Specifically, the ultrasonic probe 2B rotationally drives the first and second motors in the drive section 12 simultaneously in synchronization with each other, so that the ultrasonic transducer 2a can transmit/receive ultrasonic waves and perform a helical scan a three-dimensional region in an inspection object. As a result, the apparatus main body 3B can obtain a large number of two-dimensional tomograms varying in the coordinate position in the Z-axis direction from one position to another little by little, and thereby a three-dimensional image can be constructed from these two-dimensional tomograms. In the ultrasonic probe 2B, its drive section 12 is connected to the apparatus main body 3B by the cable 12a.

The apparatus main body 3B comprises ultrasonic observation section 31 that transmits/receives ultrasonic signals to/from the ultrasonic transducer 2a to obtain ultrasonic echo data in a three-dimensional region; an image processing section 33B that is used for obtaining ultrasonic image data based on ultrasonic echo data obtained by the above-described ultrasonic observation section 31, and that has a CPU generating ultrasonic images (three-dimensional images) based on an ultrasonic image generating method and ultrasonic image generating program each described later.

Figure 25:
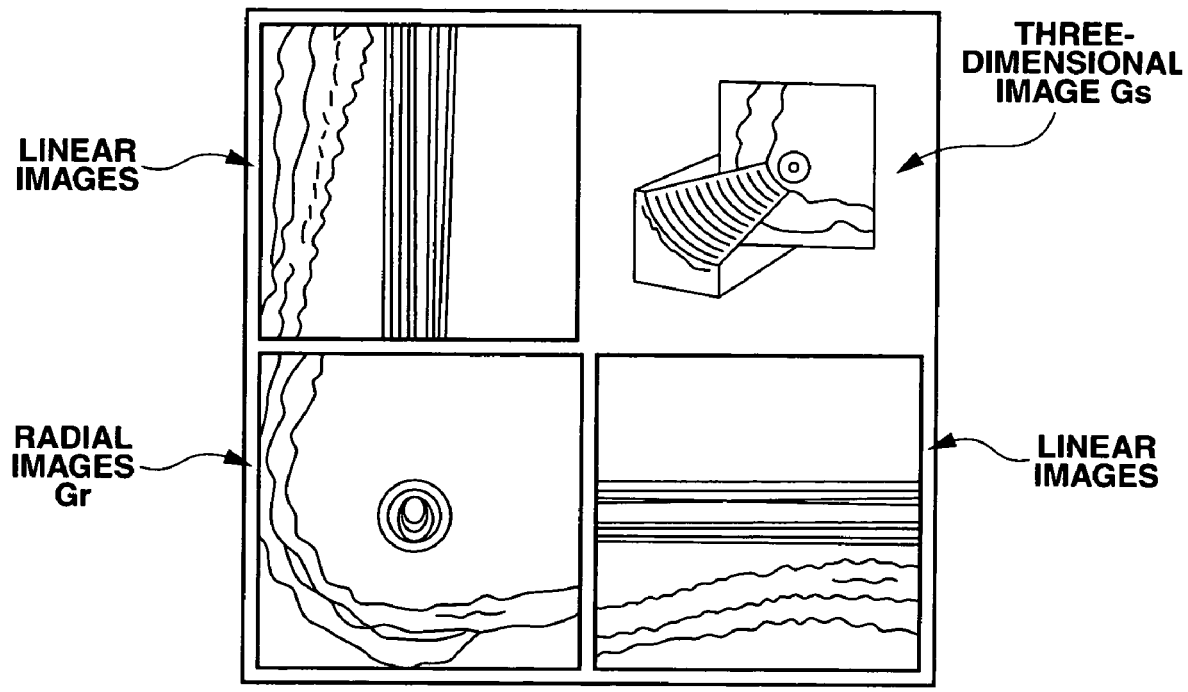
FIG. 25 is a first ultrasonic image example that has been conventionally obtained.
Figure 26:
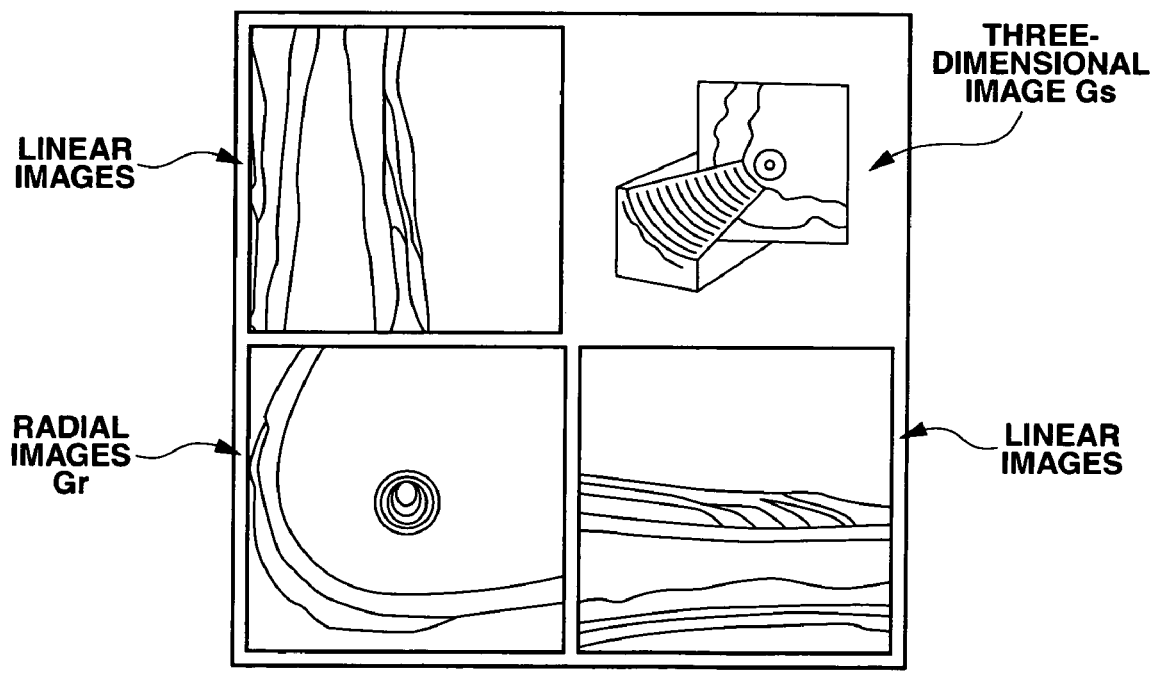
FIG. 26 is the first ultrasonic image example subjected to processing based on the flowchart in FIG. 23.

Connected to the image processing section 33B through an interface (not shown), is a mouse 34 serving as screen operating means for allowing images as shown in FIGS. 25 and 26 to be operated in an interactive manner. The mouse 34 has a function of performing a screen operation using a mouse cursor with respect to image information displayed on the display screen of the monitor 4.

The image processing section 33B has a function as control means for moving a selected operation object relative to the movement of the mouse 34, based on the selection of the operation object in a screen operation by the mouse 34. Also connected to the image processing section 33B, is a large-capacity external storage device (not shown) for recording image data or the like through an interface (not shown).

The image processing section 33B causes the ultrasonic transducer 2a to perform helical scans in predetermined pitch units; coordinate-converts ultrasonic echo data obtained in the ultrasonic observation section 31; and generate a plurality of two-dimensional radial tomograms (hereinafter referred to as radial images) Gr of cross sections substantially perpendicular to the axial direction (Z-axis direction) of the insertion section 11, for example, as shown in the left lower portion of FIG. 25. These generated radial images Gr correspond to, for example, an ultrasonic tomographic plane 20A in a stomach 20 shown in FIG. 13.

Then, the image processing section 33B generates a pseudo ultrasonic image (three-dimensional image) Gs, for example, as shown in the right upper portion of FIG. 25, based on a plurality of radial images Gr consecutively obtained in pre-determined pitch units. In FIG. 25, images displayed on the upper side of the radial image Gr and images displayed on the lower side of the ultrasonic image (three-dimensional image) Gs are linear images of cross sections substantially horizontal to the axial direction (Z-axis direction) of the insertion section 11, the linear image being generated based on the above-described radial images Gr.

In the radial images Gr shown in FIG. 25, when an organ moves under the influence of pulsation, the positions of a region of interest cause deviations between the scan starting time and scan finishing time. In the linear images shown in FIG. 25, image fluctuations like jaggies occur in the organ, thus bringing about no clear image. Consequently, an ultrasonic image (three-dimensional image) Gs as shown in FIG. 25 becomes distorted.

With this being the situation, this embodiment is configured to eliminate the influence of pulsation by the ultrasonic image generating method and ultrasonic image generating program described below.

First, surface extraction processing will be explained.

Figure 14:
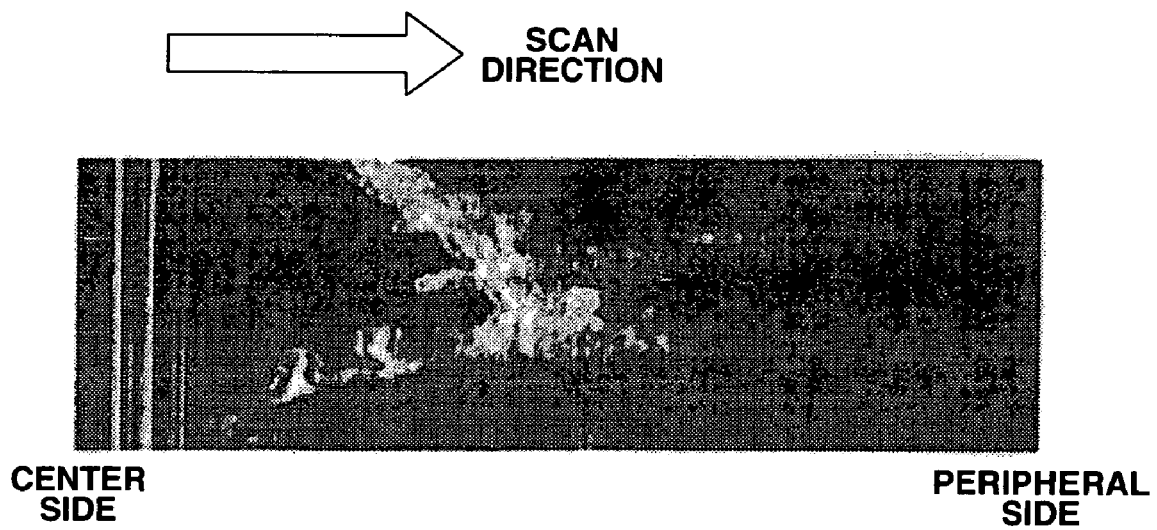
FIG. 14 is a schematic view showing a sound ray when scanning a surface position of a body cavity surface.

The surface extraction processing refers to processing for making the identification between water such as ultrasonic propagation media and bodily fluids, and living body tissues. Here, the above-described radial image Gr comprises, for example, several hundreds of sound rays (line data), and is represented by echo luminance of these sound rays. As shown in FIG. 14, a search is performed by each of the sound rays from the probe center (ultrasonic transducer) in the peripheral direction, and thereby searches for the portion at which water changes places with a living body tissue. In order to enhance the accuracy of this search, the following processing is performed.

Out of all sound rays amounting to 512 or 1024 rays, a predetermined number of sound rays are sampled to create a histogram, and then the histogram is smoothed.

For example, when the number of all sound rays is 512, the above-described smoothing is performed by the gradation of echo luminance, as shown in Table 2.

TABLE 2

| Number of pieces of sample data | Calculation is performed using 64 sound rays out of 512 sound rays |
|---|---|
| Original Gradation | 0 (low reflection) to 255 (strong reflection) |
| Gradation after Smoothing | 0 (low reflection) to 15 (strong reflection) |

Here, original gradation 0 (low reflection) to 255 (high reflection) is divided into 0 (low reflection) to 15 (high reflection) to perform smoothing.

Figure 15:
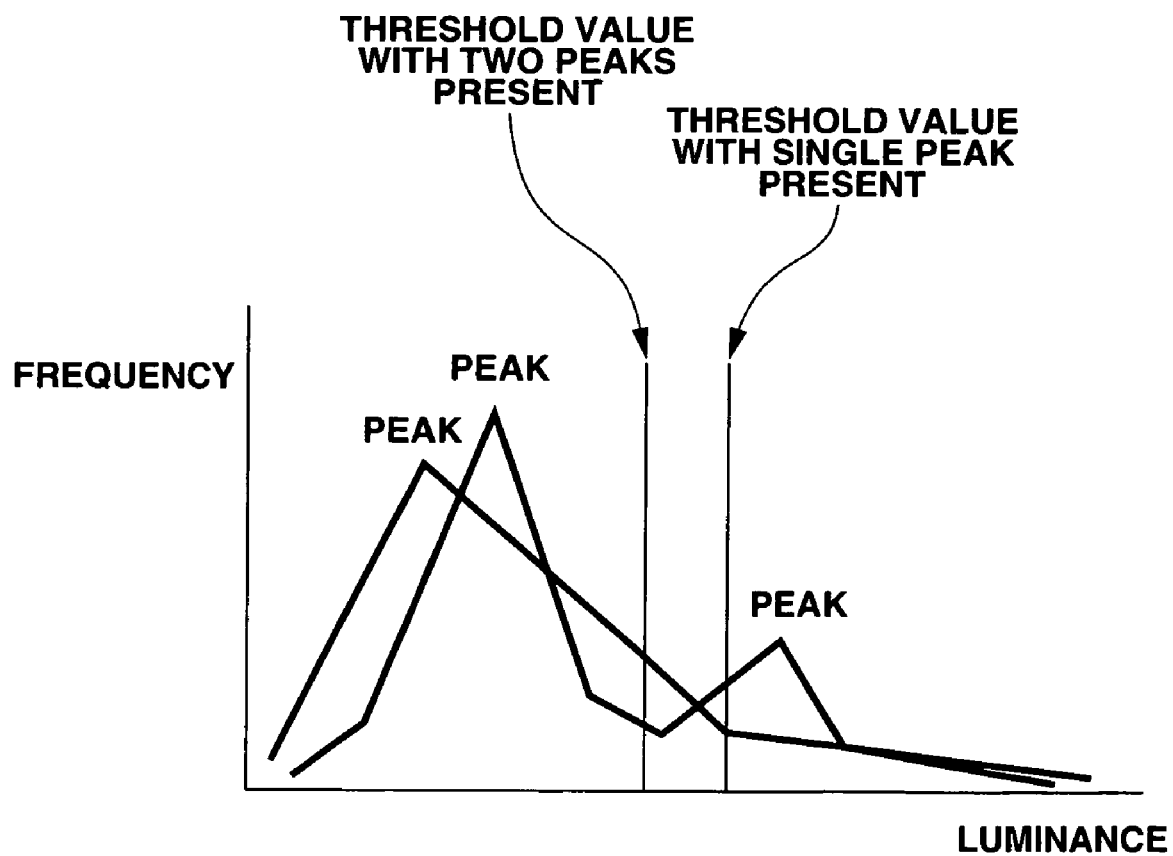
FIG. 15 is a histogram showing the frequency with respect to the luminance produced by sampling a predetermined number of sound rays with respect to all sound rays.

As a result, a histogram shown in FIG. 15 is obtained.

Next, a peak or peaks in the above-described histogram is/are determined.

The peak(s) is/are determined from the derivative values (gradients) and absolute values (heights) of the points on the graph. Usually, the peaks on the histogram include the following two patterns.

(1) Two Peaks Appear.

The two peaks indicate a water portion and a tissue portion. The threshold value, therefore, is assumed to be an intermediate value between these two peaks.

(2) A Single Peak Appears.

For a low-contrast image, only one peak (corresponding to a tissue) appears in many cases. In this case, the threshold value is assumed to be an intermediate value between the peak value and the maximum luminance value.

Here, when the threshold value 80 in an original gradation 0 to 255 (the threshold value in smoothed gradation is approximately 5) is exceeded, discrimination between water and a living body tissue cannot be satisfactorily made in many cases. Accordingly, the upper limit of threshold is assumed to be 80, and when the peak value exceeds 80, it is rounded down to 80.

If we simply determines a substance having a gradation of not more than the threshold value as water, and determines a substance having a gradation of not less than the threshold value as a living body tissue, various noise sources including suspended substances in a body cavity can be misidentified as a living body tissue.

The most typical method for removing the above-described noises is frame correlation. However, in this embodiment, in order to avoid the smoothing of an image itself to the extent possible, the determination is made by measuring the thickness of an object.

The actually misidentified noise occurs when the object has a thickness of not more than 0.2 mm.

Hence, a definite thickness is set, and when the object has a thickness of not less than the set value, the object is determined as a living body tissue. If the set value is too small, erroneous extractions increase, while if the set value is too large, a laminar structure of living body tissue is erroneously determined as noise.

Figure 16:
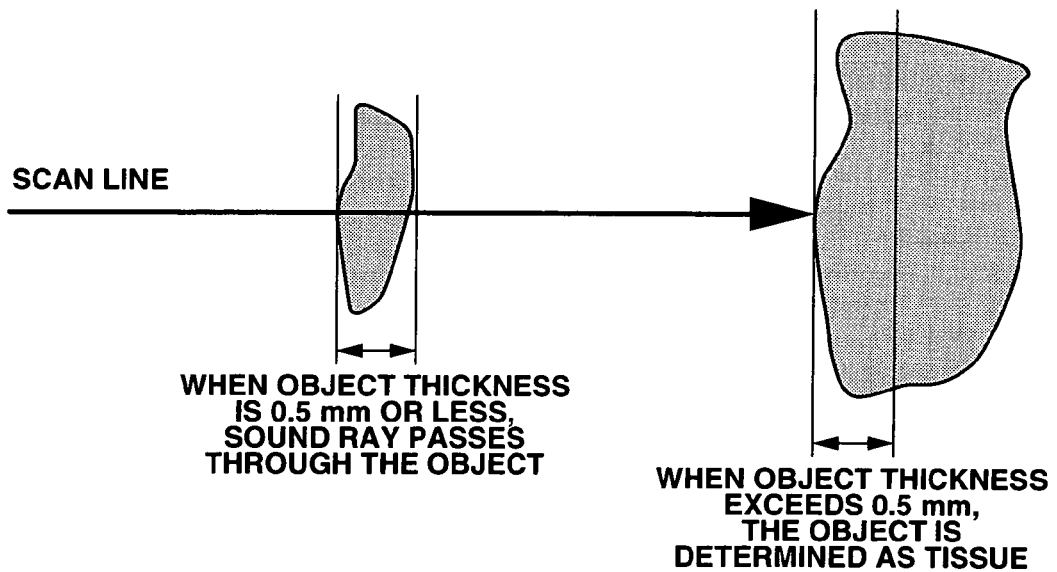
FIG. 16 is a first schematic view when determining an object as a living body tissue with respect to a scan line by a sound ray.

In this embodiment, as shown in FIG. 16, when the thickness of an object is on the order of 0.5 mm, this object is determined as a living body tissue. This method is effective for minute noise, but ineffective for noise in a broad sense, i.e., noise actually having a thickness to a certain extent, such as suspended substances in a body cavity.

Figure 17:
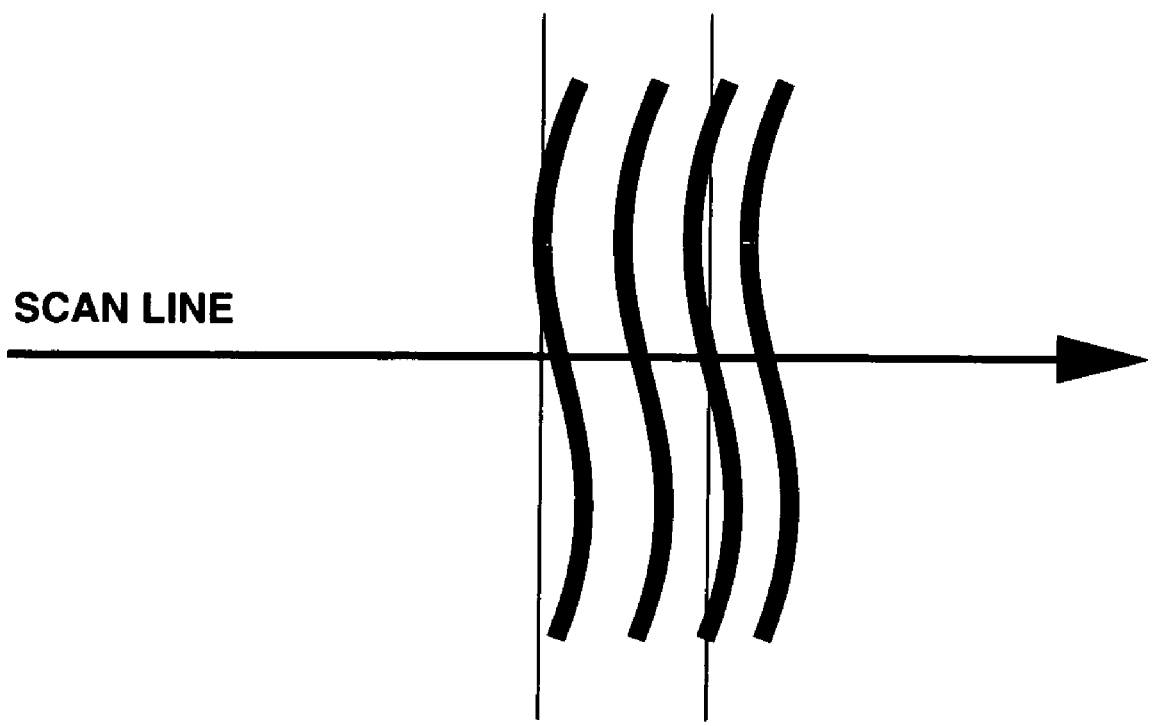
FIG. 17 is a second schematic view when determining an object as a living body tissue with respect to a scan line by a sound ray.

This being the case, as shown in FIG. 17, the determination is made by assuming the presence of a laminar structure of living body tissue.

This determination method is such that the average luminance of a definite thickness of an object is determined and that, when the determined average luminance is not less than the threshold, this object is determined as a living body tissue.

In this embodiment, the thickness of an object of which the average luminance is to be determined is assumed to be on the order of 2 mm, and when the average luminance of the thickness on the order of 2 mm is not less than the threshold, this object is determined as a living body tissue.

However, even if a body cavity surface is extracted by the above-described surface extraction processing, erroneous extractions cannot be completely eliminated. It is therefore necessary to detect possible erroneous extractions and correct them.

In this embodiment, regarding a target extraction point, the distance thereto from the probe center (ultrasonic transducer) is compared with the distances of sound rays that are prior to and subsequent to the extraction point, and thereby correction processing with respect to an erroneous extraction is performed.

Figure 18:
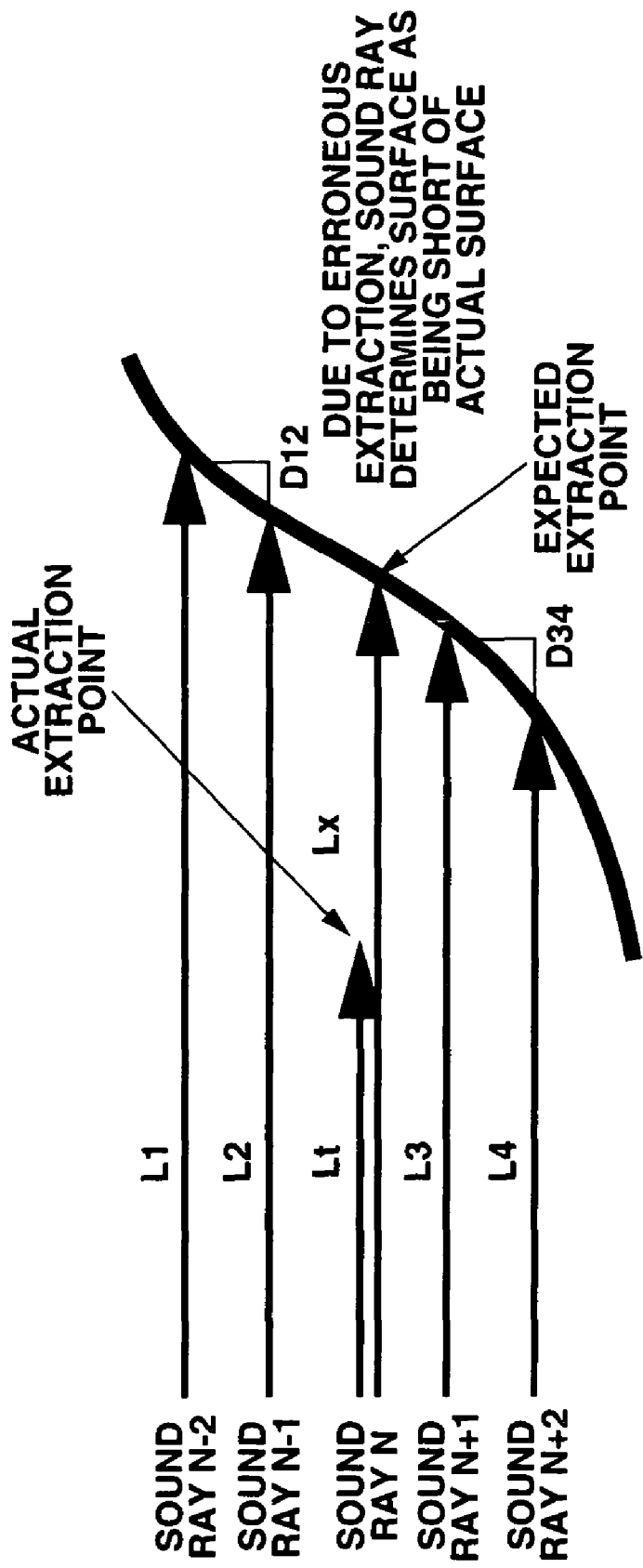
FIG. 18 is a schematic view showing a correction processing for erroneous extraction.

Specifically, as shown in FIG. 18, distance differences are calculated regarding four points that are prior to and subsequent to the extraction point, and the correctness of the target point is estimated based on the tendency of the calculation result. Here, let the actual extraction point of a sound ray N be Lt.

Due to an erroneous extraction, the sound ray N determines a body cavity surface as being short of the actual body cavity surface.

Such being the case, based on four sound rays that are prior to and subsequent to the sound ray N, that is, N−2, N−1, N+1, and N+2, an expected extraction point Lx of the sound ray N is calculated.

Letting L be the length of a sound ray, D be the difference from a subsequent sound ray N, the expected extraction point Lx is expressed by the following expression:

$$Lx=(L1+L2+Lt+L3+L4)/5+(D12+D2t+Dt3+D34)/4$$

where,
L1=the length of the sound ray (N−2)
L2=the length of the sound ray (N−1)
L3=the length of the sound ray (N+1)
L4=the length of the sound ray (N+2)
D12=the difference between the sound ray (N−2) and sound ray (N−1)
D2t=the difference between the sound ray (N−1) and sound ray N
Dt3=the difference between the sound ray N and sound ray (N+1)
D34=the difference between the sound ray (N+1) and sound ray (N+2)

Here, the average between the D12 and D34 indicates an increasing/decreasing tendency of the distance from the probe center (ultrasonic transducer) to the body cavity surface.

A value obtained by adding this tendency to an average surface distance, constitutes an expected extraction point of an target point.

The erroneous extraction point is short of the body cavity surface, or located behind it. Hence, the expected extraction point Lx and actual extraction point Lt are compared with each other, and if the actual extraction point Lt is 3 mm or more apart from the expected extraction point Lx that has been calculated, the actual extraction point Lt is replaced with the expected extraction point Lx that has been calculated, whereby an erroneous extraction is corrected. While not illustrated, the correction processing for the erroneous extraction may be arranged so that the expected extraction point Lx of the sound ray N is calculated based on six sound rays that are prior to and subsequent to the sound ray N, that is, N−3, N−2, N−1, N+1, N+2, and N+3.

Next, based on the body cavity surface determined in the above-described correction processing for erroneous extraction, body cavity center calculation processing for calculating the body cavity center as a reference position, is performed.

In this embodiment, the body cavity surface extracted is converted from the polar coordinates (sound ray number and distance) into the Cartesian coordinates, and the body cavity center is determined from the surface distance (i.e., the distance from the probe center (ultrasonic transducer) to the extraction point) of sound rays clockwise disposed at positions of 3, 6, 9, and 12 o'clock on this Cartesian coordinates. Specifically, the body cavity center (X, Y) is given by the following expressions.

$$X=(|X\text{-coordinate of the surface extraction point in the 3 o'clock direction}|+|X\text{-coordinate of the surface extraction point in the 9 o'clock direction}|)/2$$

$$Y=(|Y\text{-coordinate of the surface extraction point in the 12 o'clock direction}|+|Y\text{-coordinate of the surface extraction point in the 6 o'clock direction}|)/2$$

Figure 19:
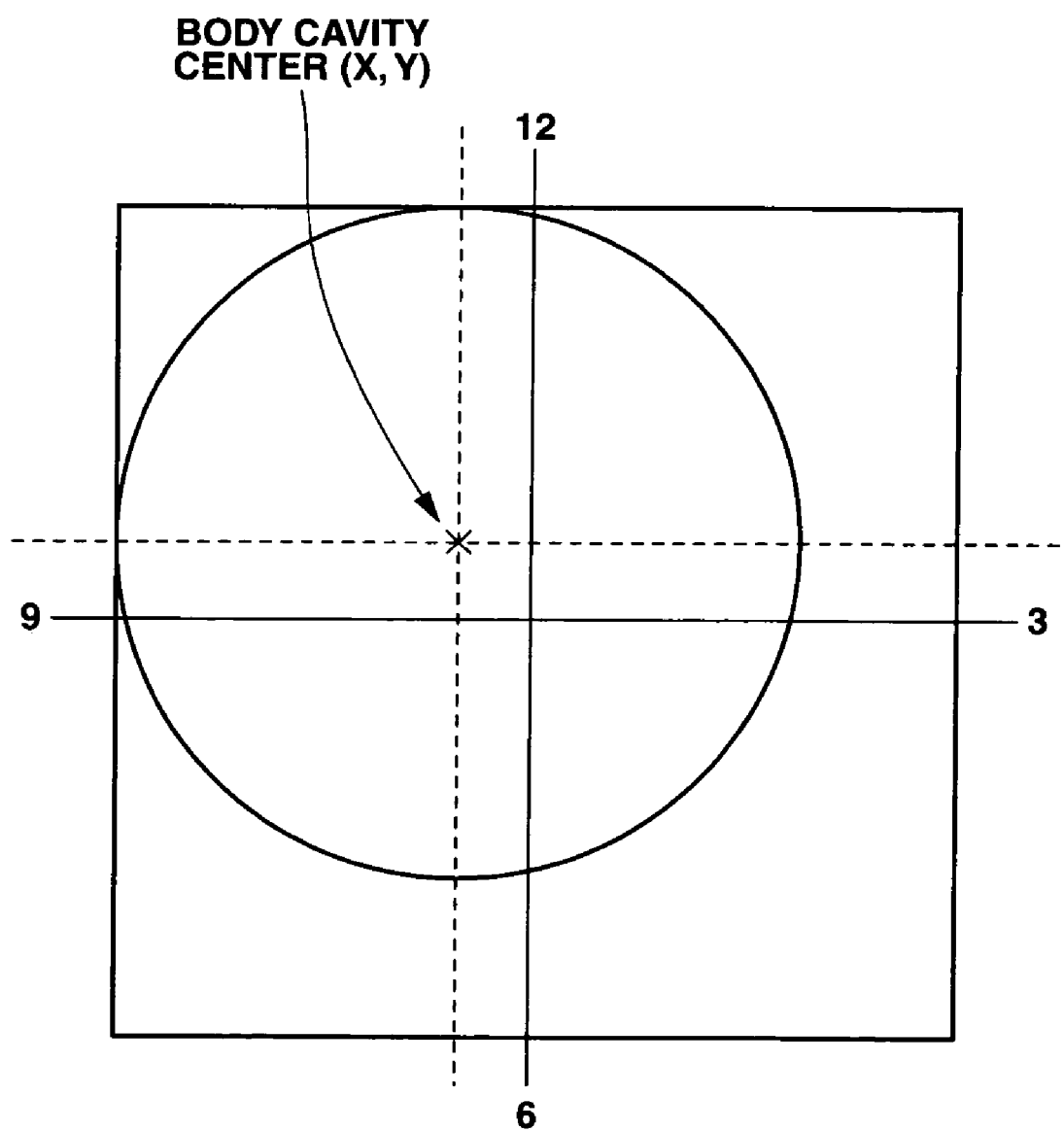
FIG. 19 is a first explanatory diagram showing a concrete example for determining the body cavity center (X, Y) as a reference position.
Figure 20:
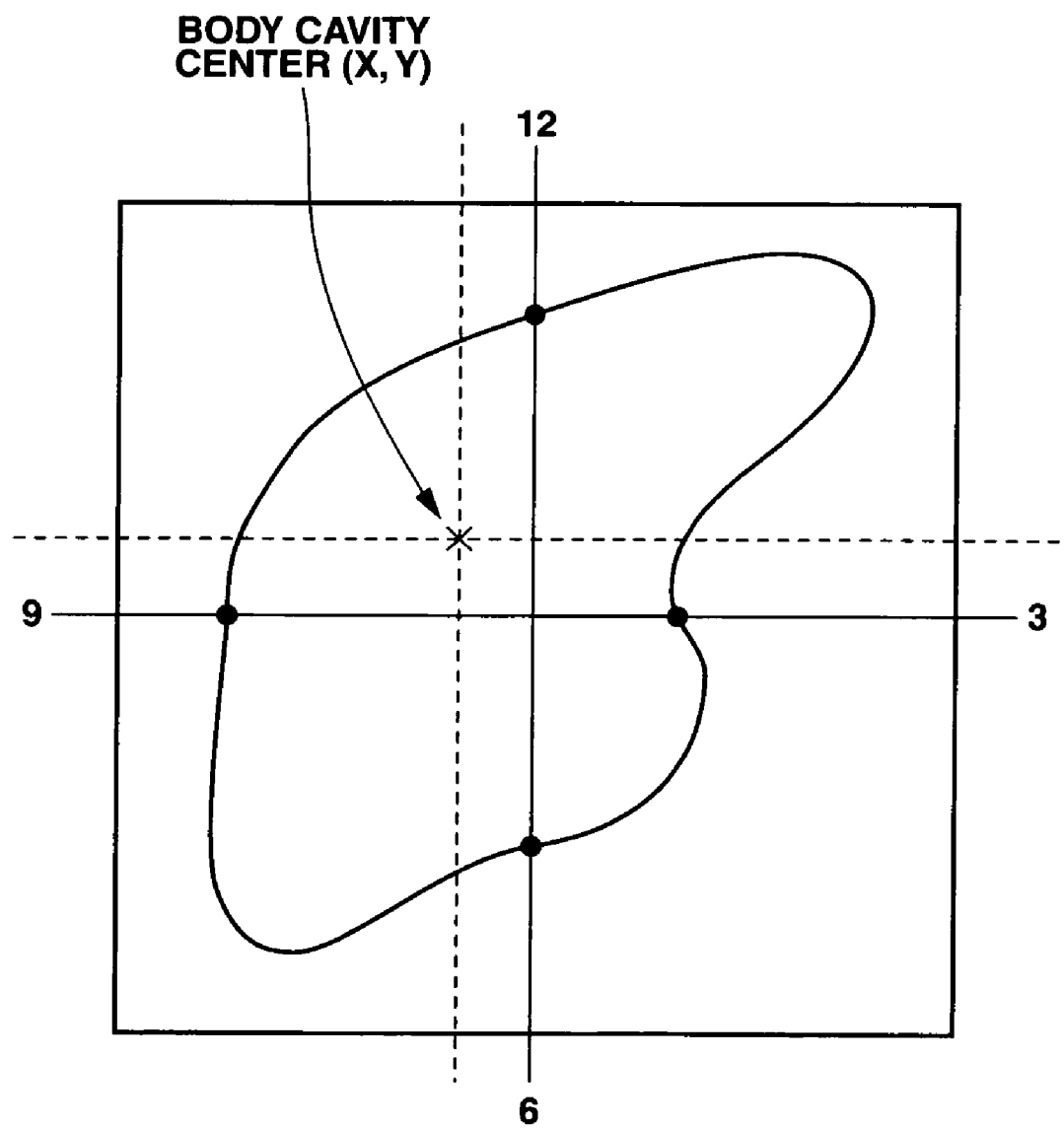
FIG. 20 is a second explanatory diagram showing a concrete example for determining the body cavity center (X, Y) as a reference position.

For example, in the case of a body cavity surface having a substantially circular form as shown in FIG. 19, the body cavity center (X, Y) takes the position marked with "x" indicating the center of the substantial circle. Also, in the case of a body cavity surface having a substantially rhombic shape as shown in FIG. 20, the body cavity center (X, Y) takes the position marked with "x" indicating the center of the substantial rhombus. While not illustrated, there is a case where the calculated body cavity center (X, Y) exists outside the living body tissue.

After the body cavity center calculation processing, as described in the first embodiment, processing is performed for shifting each of the plurality of radial images Gr to adjust the positions of these images, and causing the body cavity centers (X, Y) determined in the above-described body cavity center processing for each of the images, to coincide with each other.

Next, as described in the first embodiment, by using prior and subsequent images, processing is performed for smoothing the surface extraction points (already converted into the Cartesian coordinate values) of a predetermined radial image Gr sandwiched by these images, in the Z-axis direction (longitudinal direction), and thereby smoothing the positions of the body cavity surfaces.

Figure 21:
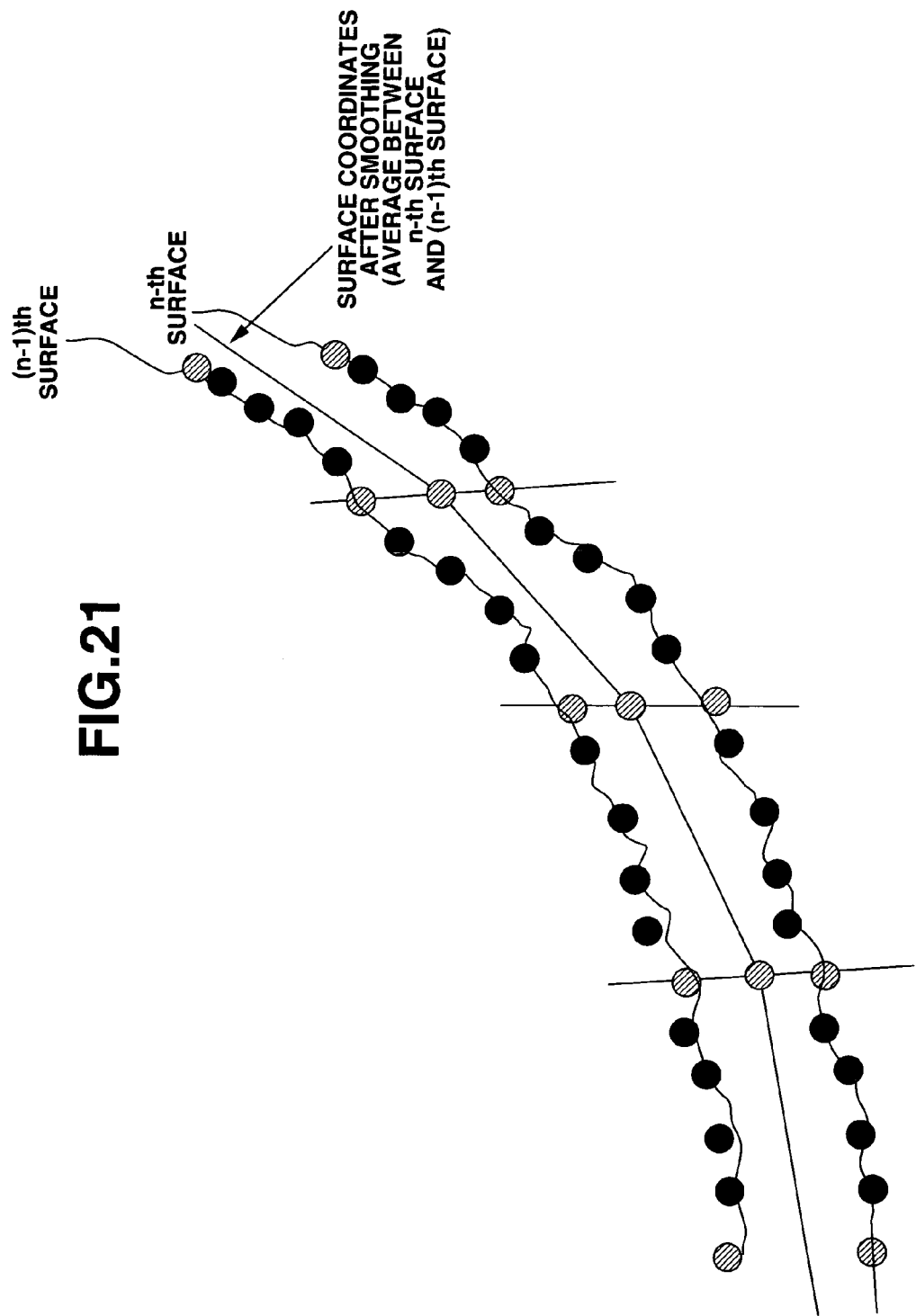
FIG. 21 is a schematic view showing processing for smoothing the positions on a body cavity surface using prior and subsequent images.

As shown in FIG. 21, in this embodiment, the smoothing (averaging) of the surface positions of the radial image Gr is performed by using surface extraction points of the n-th surface and the (n−1)th surface of the radial image Gr. Here, for example, regarding the number of surfaces of the radial images Gr to be referred to for smoothing, as many surfaces as exist within the range of 2 mm in the Z-axis direction, i.e., longitudinal direction (8 surfaces for 0.25 mm pitch, and 4 surfaces for 0.5 mm pitch) are used to perform averaging, whereby the surface positions of the body cavity surface are smoothed.

Thus, in the case of a three-dimensional model display (surface display), it is possible to construct smooth body cavity surfaces that are even more natural and smooth by utilizing smoothed coordinate values.

After the above-described smoothing, as described in the first embodiment, the processing is performed for calculating the differences between the surface positions of the body cavity surface before smoothing (i.e., the positions of the extracted body cavity surface) and the surface positions of the smoothed body cavity surface so that the surface positions of the body cavity surface before the smoothing (the extracted body cavity surface) and the surface positions of the smoothed body cavity surface mutually coincide, and then the processing is performed for expanding/contracting a predetermined radial image Gr based on the above-described calculated differences.

Figure 22:
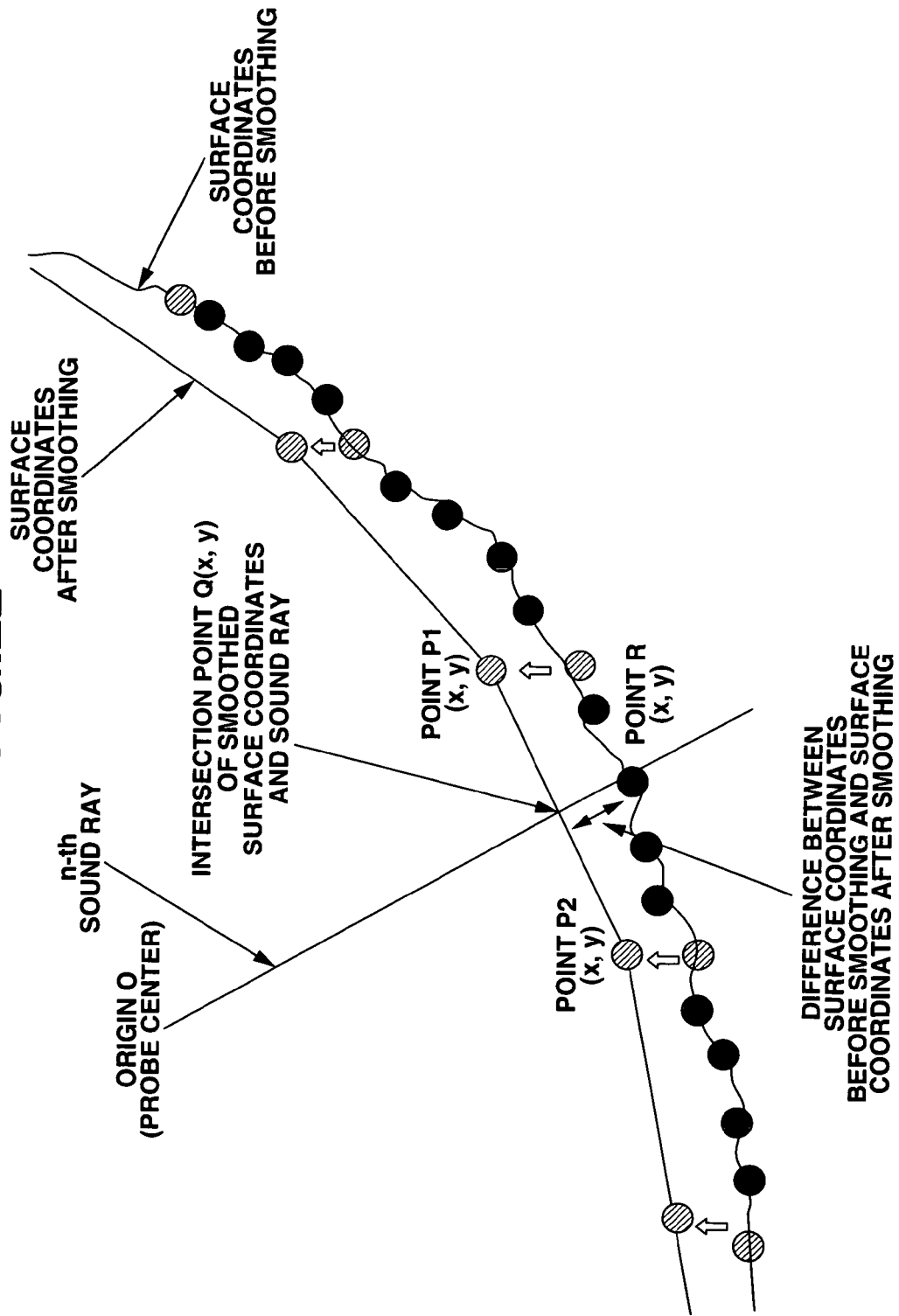
FIG. 22 is a schematic view when distance correction processing is performed so that sound ray data is converted into radial images, and that the surface positions of the body cavity surface before smoothing (i.e., surface coordinates before smoothing) coincide with the surface positions of the smoothed body cavity (i.e., surface coordinates after the smoothing).

As shown in FIG. 22, in this embodiment, sound ray data is converted to radial image and distance correction processing is performed so that the surface positions of the body cavity surface before smoothing (i.e., the surface coordinates before the smoothing) and the surface positions of the smoothed body cavity surface (i.e., the surface coordinates after the smoothing) mutually coincide.

The distance correction processing is performed in accordance with the following procedure.

First, the distance differences are calculated between the surface positions of the smoothed body cavity surface (i.e., surface coordinates after smoothing) and the surface positions (surface coordinates) of the body cavity surface before the smoothing (i.e., surface coordinates before the smoothing). Thereby, the distances D are calculated between the surface positions of the body cavity surface before the smoothing (i.e., the surface coordinates before the smoothing) and the surface positions of the smoothed body cavity surface (i.e., the surface coordinates after the smoothing).

This distance D is determined from the point R of intersection between the n-th sound ray and the surface position of the body cavity surface before smoothing (i.e., the surface coordinates before the smoothing), and the point Q of intersection between the n-th sound ray and the surface position of the smoothed body cavity surface (i.e., the surface coordinates after the smoothing).

Here, let the origin of the probe center (ultrasonic transducer) be O, and let a line segment between surface positions (surface coordinates after smoothing) on a smoothed body cavity surface be P1P2, the surface coordinates including an point Q of intersection with a straight line OPn. Then, the intersection point Q (x, y) can be determined from the following expressions:

(1) Preconditions:

$a1 = Pn.y/Pn.x$ $b1 = 0$ $a2 = (P2.y - P1.y)/(P2.x - P1.x)$ $b2 = (P1.y - (P2.y - P1.y)/(P2.x - P1.x) \times P1.x)$ (2) Coordinates of the intersection point Q $Q.x = (b2 - b1)/(a1 - a2)$ $Q.y = a1 \times (b2 - b1)/(a1 - a2) + b1$ where, R=Pn From the above-described intersection points Q and intersection point R, the difference D between these intersection points Q and R can be calculated.

Next, based on the calculated difference D, processing for expanding/contracting a predetermined radial image Gr is performed.

Here, a point on sound ray data that determines one arbitrary point P(x, y) on the radial image Gr is determined by the following expression:

(1) Preconditions:

$T = 2\pi/512 \times$ sound ray number (N=0 to 512)

L=distance from the origin O to the body cavity surface, D=difference (2) Coordinates of P $P.x = \cos T \times (L + D)$ $P.y = \sin T \times (L + D)$ Thus, by incorporating the distance differences D between the smoothed surface positions of the body cavity surface after smoothing (i.e., surface coordinates after the smoothing), and the surface positions of the body cavity surface before the smoothing (i.e., surface coordinates before the smoothing) into L (distance from the origin O to the body cavity surface), it is possible to conform the surface positions of the smoothed body cavity surface (i.e., surface coordinates after the smoothing) to the surface positions of the body cavity surface before the smoothing (i.e., surface coordinates before the smoothing). In other words, the processing for expanding/contracting the predetermined radial image Gr becomes achievable.

The use of the radial images Gr subjected to the distance correction processing results in the construction of linear images with the influence of pulsation reduced.

The ultrasonic image generating method and ultrasonic image generating program that have such features will be described based on flowcharts shown in FIGS. 23 and 24.

First, as described in FIG. 13, the ultrasonic probe 2B rotationally drives the first and second motors in the drive section 12 simultaneously by synchronizing them, so that the ultrasonic transducer 2a performs helical scans in predetermined pitch units.

Thereupon, in the apparatus main body 3B, ultrasonic echo signals in a three-dimensional region received by the ultrasonic transducer 2a are inputted into the ultrasonic observation section 31. The ultrasonic observation section 31 receives the ultrasonic echo signals in the three-dimensional region from the ultrasonic transducer 2a, and coordinate-converts the ultrasonic echo signals to generate a plurality of consecutive radial images Gr. Then, the image processing section 33B receives input of the pieces of image data on the radial images Gr from the ultrasonic observation section 31 one after another, thereby acquiring the plurality of consecutive radial images Gr (step S11). At this time, the image processing section 33B makes discrimination between water such as ultrasonic propagation media and bodily fluids, and living body tissues, by the surface extraction processing illustrated in FIGS. 15 to b17, thereby generating radial images Gr.

Then, as reference position setting steps for determining the reference position on each image with respect to the plurality of consecutive radial images Gr, the image processing section 33B performs the following processes of steps S12 and S13.

First, with respect to the plurality of consecutive radial images Gr, the image processing section 33B extracts surface coordinates of each of the images, and determines surface extraction points (step S12).

Figure 24:
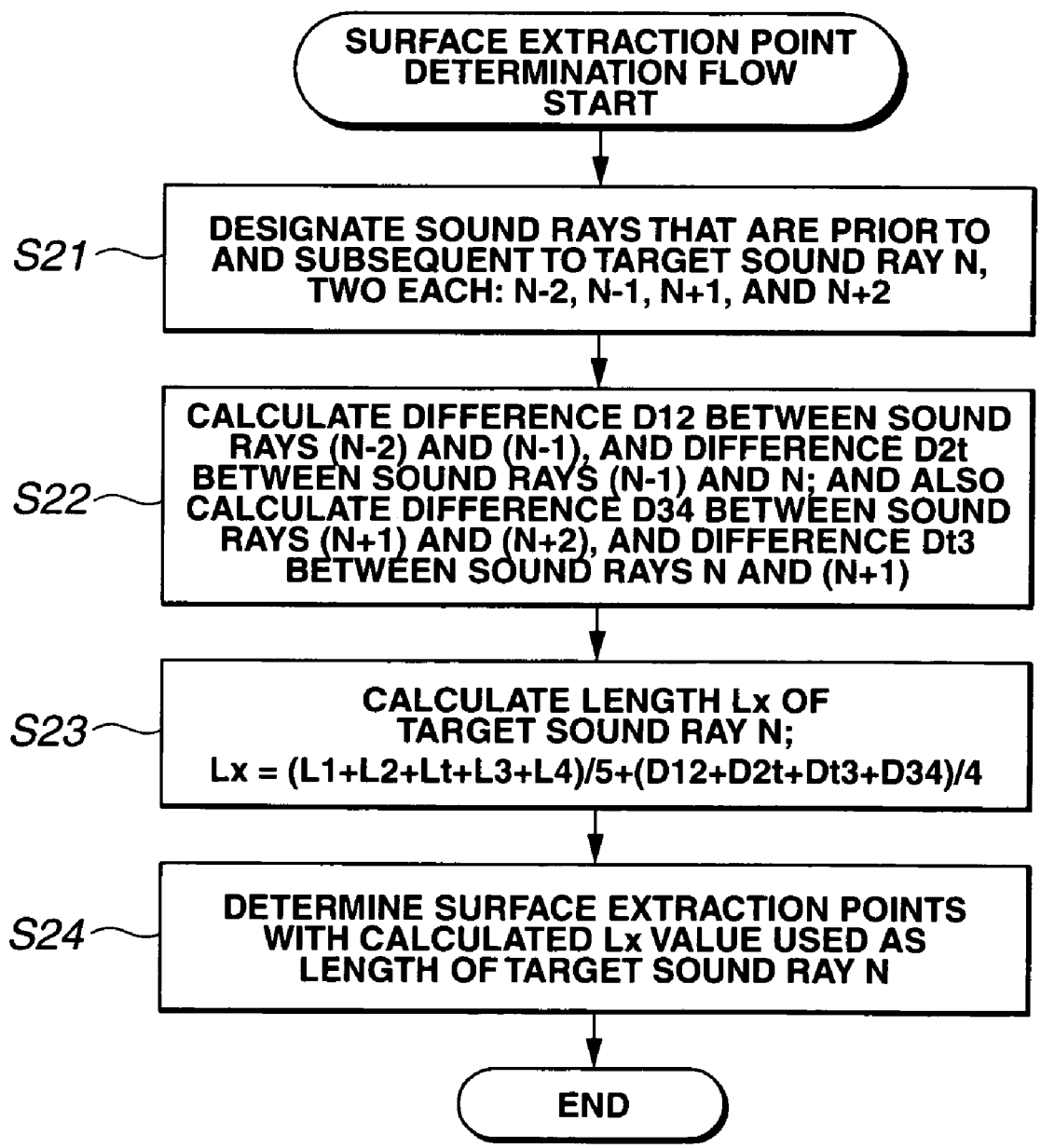
FIG. 24 is a flowchart showing a subroutine for determining the surface extraction points in FIG. 23.

Here, based on a flowchart shown in FIG. 24, the image processing section 33B determines surface extraction points by the erroneous extraction correction processing illustrated in FIG. 18.

First, sound rays that are prior to and subsequent to a target sound ray N are designated, two each: N−2, N−1, N+1, and N+2 (step S21).

Next, the difference D12 between sound rays (N−2) and (N−1), and the difference D2t between sound rays (N−1) and N are calculated, as well as the difference D34 between sound rays (N+1) and (N+2), and the difference Dt3 between the sound rays N and (N+1) are calculated (step S22), whereby the length of the target sound ray N (i.e., expected extraction point) Lx is calculated (step S23).

Here, it is determined whether an actual extraction point Lt is 3 mm or more apart from the above-described expected extraction point Lx that has been calculated. If so, the surface extraction point is determined by substituting the expected extraction point Lx for the length of the target sound ray N (step S24).

Then, the above-described correction processing is performed with respect to all sound rays amounting to 512 rays or 1024 rays.

This allows the image processing section 33B to extract surface coordinates of each of the plurality of consecutive radial images Gr.

Next, with respect to the plurality of consecutive radial images Gr, the image processing section 33B determines a body cavity center as a reference position on each of the images, based on the body cavity surface coordinates determined by the above-described correction processing for erroneous extraction (step S13). Herein, the image processing section 33B determines the reference position by the body cavity center calculation processing illustrated in FIGS. 19 and 20.

Here, as described above, when the polar coordinates (sound ray number and distance) have been converted into the Cartesian coordinates, the image processing section 33B calculates the body cavity center, based on surface distances (distance from the probe center (ultrasonic transducer) to an extraction point) of sound rays disposed clockwise at the positions of 3, 6, 9, and 12 o'clock.

Since the above-described body cavity center calculation processing calculates the body cavity center only at four positions of 3, 6, 9, and 12 o'clock, far less steps for making calculation is required in the second embodiment than in the above-described first embodiment in which a polygon formed by connecting surface extraction points is generated to determine a barycenter as a reference position. This allows the calculation time to be shorter, and the reference position to be rapidly calculated. Thereby, in the second embodiment, the reference position can be more quickly calculated than in the first embodiment, resulting in the achievement of speedup.

After the body cavity center calculation processing, as described in the first embodiment, the image processing section 33B performs processing for shifting each of the plurality of radial images Gr to adjust the positions of these images, and causing the body cavity centers (X, Y) determined in the above-described processing for each of the images, to mutually coincide.

Next, as illustrated in FIG. 21, the image processing section 33B uses prior and subsequent images to perform processing for smoothing the surface extraction points of a predetermined radial image Gr sandwiched by these images, in the Z-axis direction (longitudinal direction), and thereby performs the processing for smoothing the positions of the body cavity surfaces (step S15).

After the above-described smoothing, as described in the first embodiment, the image processing section 33B performs processing for calculating the differences between the surface positions of the body cavity surface before the smoothing (i.e., the positions of the extracted body cavity surface) and the surface positions of the smoothed body cavity surface so that the surface positions of the body cavity surface before smoothing (the positions of extracted body cavity surface) and the surface positions of the smoothed body cavity surface mutually coincide, and then performs processing for expanding/contracting a predetermined radial image Gr based on the above-described calculated differences.

By the procedure illustrated in FIG. 22, the image processing section 33B performs distance correction processing so that the surface positions of the body cavity surface before smoothing (i.e., the surface coordinates before the smoothing) coincide with the surface positions of the smoothed body cavity surface after the smoothing (i.e., the surface coordinates after the smoothing), whereby the surface positions of the smoothed body cavity surface (i.e., the surface coordinates after the smoothing) is conformed to the surface positions of the body cavity surface before the smoothing (i.e., the surface coordinates before the smoothing). Thus, in the second embodiment, the use of the radial images Gr subjected to the above-described distance correction processing results in the construction of linear images with pulsation reduced.

Figure 27:
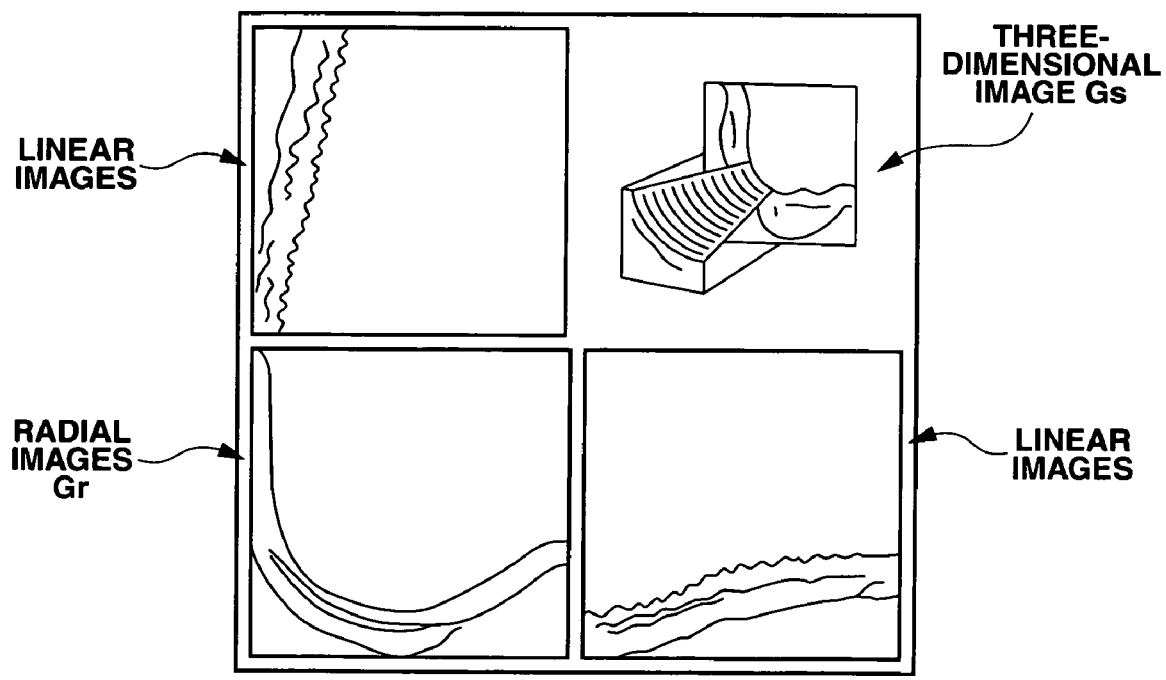
FIG. 27 is a second ultrasonic image example that has been conventionally obtained.
Figure 28:
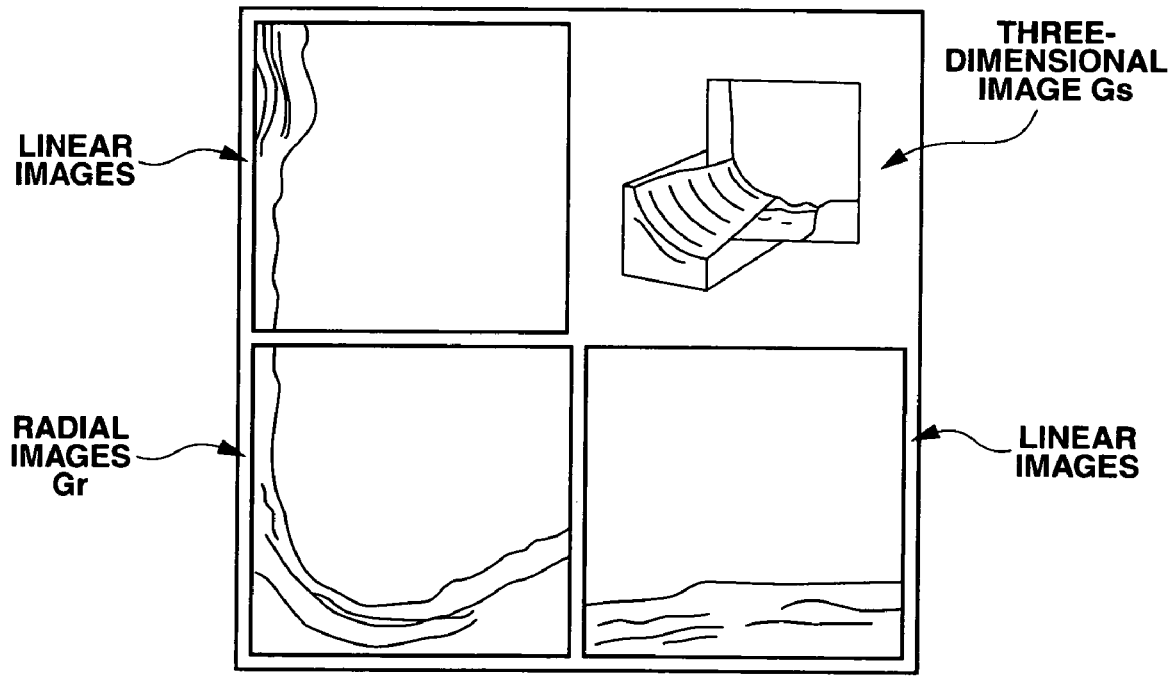
FIG. 28 is the second ultrasonic image example subjected to processing based on the flowchart in FIG. 23.

Here, the radial images Gr and linear images shown in FIGS. 26 and 28 become free of fluctuations (jaggy portions on a body cavity surface) due to pulsation, and exhibit clear body cavity surfaces as compared with the radial images Gr and linear images shown in FIGS. 25 and 27, respectively.

Then, the image processing section 33B obtains the consecutive radial images Gr corrected in the correction steps (S14 to S17), and performs an ultrasonic image generating step (step S18) for generating an ultrasonic image (three-dimensional image) based on these consecutive radial images Gr.

Thereby, the image processing section 33B can generate ultrasonic images (three-dimensional image) Gs, shown in FIGS. 26 and 28, having smooth body cavity surfaces as compared with ultrasonic images (three-dimensional image) Gs shown in FIGS. 25 and 27, respectively.

Figure 23:
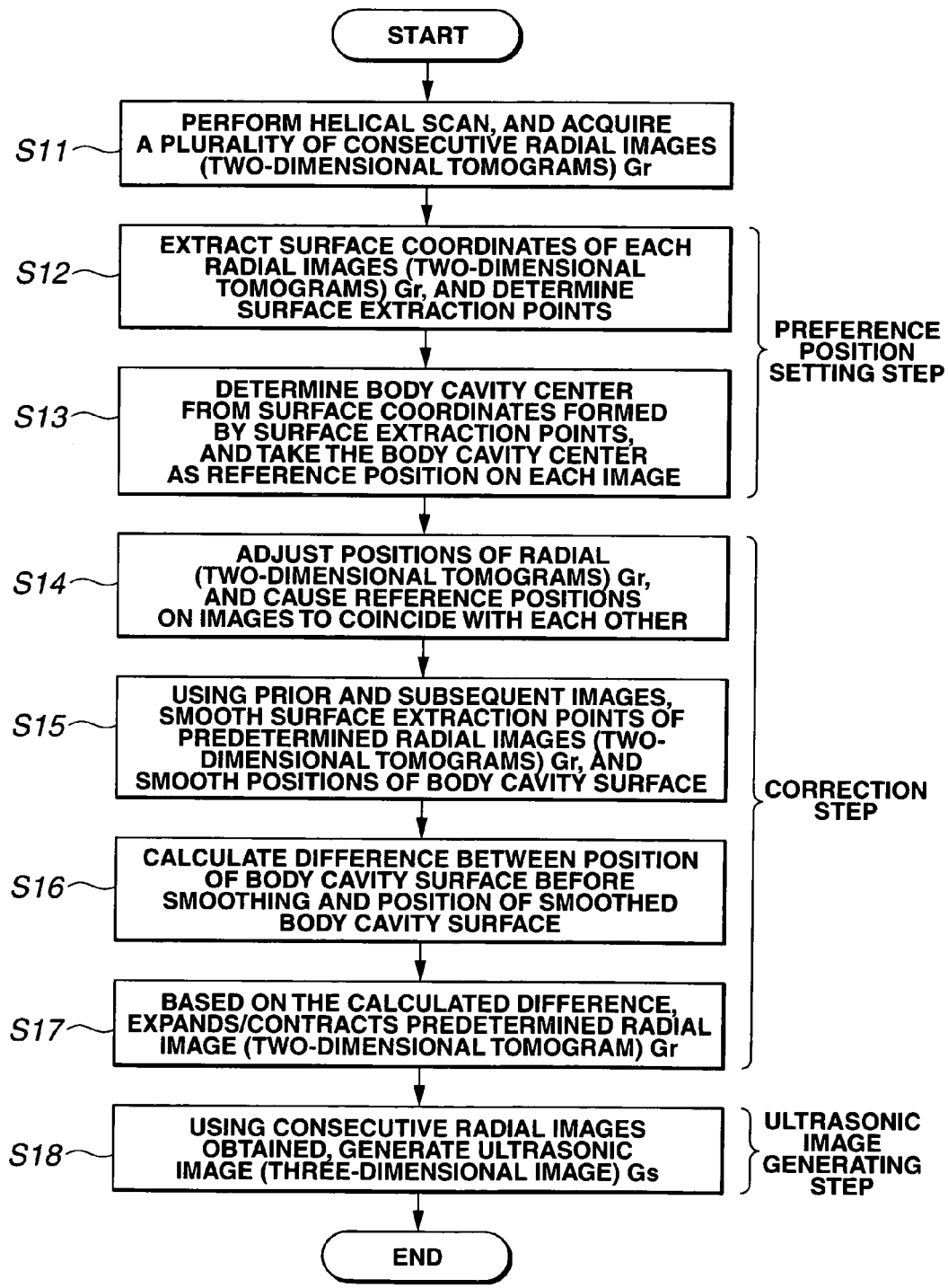
FIG. 23 is a flowchart showing an ultrasonic image generating method in an ultrasonic diagnostic system according to a second embodiment.

FIGS. 25 and 27 are examples of ultrasonic images conventionally obtained, while FIGS. 26 and 28 are examples of ultrasonic images subjected to the processing based on the flowchart in FIG. 23. Here, FIGS. 27 and 28 are images each cleared of multi-echo portions as compared with FIGS. 25 and 26.

As in the case of the above-described first embodiment, the ultrasonic image generating method and ultrasonic image generating program according to the second embodiment can be utilized not only during an ultrasonic inspection, but also when stored data is reproduced after the ultrasonic inspection for an image review for a therapeutic policy in the future, or for volume measurement.

As a result, the ultrasonic image generating method and ultrasonic image generating program according to the second embodiment can acquire high-quality and distortion-free two-dimensional tomograms and ultrasonic images (three-dimensional images) that are even more unsusceptible to pulsation than those acquired in the above-described first embodiment.

The present invention is not limited to the above-described embodiments, but various modifications may be made without departing from the spirit and scope thereof.

Embodiments constructed by partially combining the above-described embodiments are also subsumed under the present invention.

It is obvious that the present invention is not limited to the above-described embodiments, but that various modifications and applications are possible without departing from the spirit and scope thereof.

What is claimed is:

1. An ultrasonic image generating method for generating an ultrasonic image based on ultrasonic echo data obtained by transmitting ultrasonic waves to and receiving ultrasonic waves from an inspection object, the method comprising:

a surface extraction step for obtaining, on a plurality of consecutive two-dimensional tomograms obtained in accordance with the ultrasonic echo data, positions where an average luminance at a constant thickness of an object on the two-dimensional tomograms is equal to or greater than a predetermined value as extraction points on a surface inside a body cavity, based on a luminance of the two-dimensional tomograms and the thickness of the object;

an extraction point correction step for calculating expected extraction points based on a result of obtaining other extraction points adjacent to the extraction points and then correcting the extraction points using the expected extraction points;

a reference position determining step for performing, using a computer, a processing for converting surface coordinate in accordance with the extraction points corrected by the extraction point correction step from polar coordinates to Cartesian coordinates, and then calculating a center position of the body cavity as a reference position on the two-dimensional tomograms based on coordinate values disposed clockwise at positions of 3, 6, 9, and 12 o'clock on the Cartesian coordinates;

a correction step for obtaining, using a computer, a plurality of regular and consecutive two-dimensional tomograms by correcting irregularity of the reference position of each of the plurality of consecutive two-dimensional tomograms determined by the reference position determining step; and an ultrasonic image generating step for generating, using a computer, three-dimensional ultrasonic images based on the plurality of regular and consecutive two-dimensional tomograms corrected by the correction step.

2. The computer-implemented ultrasonic image generating method according to claim 1, wherein the correction step comprises:

a shifting operation that, so as to cause a predesignated reference position of a predetermined two-dimensional tomogram and the reference position of another two-dimensional tomogram different from that of the predetermined two-dimensional tomogram to coincide with each other, includes shifting the other two-dimensional tomogram.

3. The computer-implemented ultrasonic image generating method according to claim 2, wherein the correction step further comprises:

a smoothing operation that, after having caused the predetermined reference position of the predetermined two-dimensional tomogram and the reference position of the other two-dimensional tomogram to coincide with each other, includes smoothing the positions of a body cavity surface using prior and subsequent two-dimensional tomograms sandwiching the predetermined two-dimensional tomogram.

4. The computer-implemented ultrasonic image generating method according to claim 3, wherein the correction step further comprises:

calculating, after the smoothing has been performed, the differences between the positions of the body cavity surface before the smoothing, and the positions of the smoothed body cavity surface; and expanding/contracting pertinent two-dimensional tomograms based on the calculated differences, and thereby obtaining a consecutive ultrasonic image.

5. The ultrasonic image generating method according to claim 1, wherein the plurality of consecutive two-dimensional tomograms used in determining the reference position are a plurality of consecutive two-dimensional radial images that are obtained by helically scanning the inspection object in predetermined pitch units.

6. The ultrasonic image generating method according to claim 1, wherein irregularity of the reference position occurs accompanying pulsation of the inspection object.

7. One or more non-transitory computer-readable storage media having stored thereon a computer program for generating an ultrasonic image based on ultrasonic echo data obtained by transmitting ultrasonic waves to and receiving ultrasonic waves from an inspection object, that, when executed by one or more processors, causes the one or more processors to:

obtain, on a plurality of consecutive two-dimensional tomograms obtained in accordance with the ultrasonic echo data, positions where an average luminance at a constant thickness of an object on the two-dimensional tomograms is equal to or greater than a predetermined value as extraction points on a surface inside a body cavity, based on a luminance of the two-dimensional tomograms and the thickness of the object;

calculate expected extraction points based on a result of obtaining other extraction points adjacent to the extraction points and then correct the extraction points using the expected extraction points;

convert surface coordinate in accordance with the corrected extraction points from polar coordinates to Cartesian coordinates, and then calculate a center position of the body cavity as a reference position on the two-dimensional tomograms based on coordinate values disposed clockwise at positions of 3, 6, 9, and 12 o'clock on the Cartesian coordinates;

obtain a plurality of regular and consecutive two-dimensional tomograms by correcting irregularity of the determined reference position of each of the plurality of consecutive two-dimensional tomograms; and generate a three-dimensional ultrasonic image based on the plurality of corrected regular and consecutive two-dimensional tomograms.

8. One or more non-transitory computer-readable storage media as recited in claim 7, wherein to obtain regular and consecutive two-dimensional tomograms by correcting irregularity of the determined reference position of each of the two-dimensional tomograms, the one or more processors cause a predesignated reference position of a predetermined two-dimensional tomogram and the reference position of another two-dimensional tomogram different from the predetermined two-dimensional tomogram to coincide with each other, includes shifting the other two-dimensional tomogram.

9. One or more non-transitory computer-readable storage media as recited in claim 7, wherein to obtain regular and consecutive two-dimensional tomograms by correcting irregularity of the determined reference position of each of the two-dimensional tomograms, the one or more processors after having caused the predetermined reference position of the predetermined two-dimensional tomogram and the reference position of the other two-dimensional tomogram to coincide with each other, smooth the positions of a body cavity surface using prior and subsequent two-dimensional tomograms sandwiching the predetermined two-dimensional tomogram.

10. One or more non-transitory computer-readable storage media as recited in claim 7, wherein to obtain regular and consecutive two-dimensional tomograms by correcting irregularity of the determined reference position of each of the two-dimensional tomograms, the one or more processors calculate, after the smoothing has been performed, the differences between the positions of the body cavity surface before the smoothing, and the positions of the smoothed body cavity surface; and expand/contract pertinent two-dimensional tomograms based on the calculated differences, and thereby obtaining a consecutive ultrasonic image.

11. One or more non-transitory computer-readable storage media as recited in claim 7, wherein the plurality of consecutive two-dimensional tomograms used in determining the reference position are a plurality of consecutive two-dimensional radial images that are obtained by helically scanning the inspection object in predetermined pitch units.

12. One or more non-transitory computer-readable storage media as recited in claim 7, wherein irregularity of the reference position occurs accompanying pulsation of the inspection object.

* * * * *